US008778338B2

(12) United States Patent
Gass et al.

(10) Patent No.: US 8,778,338 B2
(45) Date of Patent: Jul. 15, 2014

(54) COMBINATION ENZYME THERAPY FOR DIGESTION OF DIETARY GLUTEN

(75) Inventors: Jonathan David Gass, Collegeville, PA (US); Chaitan Khosla, Palo Alto, CA (US); Michael Bethune, Pasadena, CA (US); Matthew John Siegel, Sunnyvale, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 74 days.

(21) Appl. No.: 12/531,036

(22) PCT Filed: Mar. 14, 2008

(86) PCT No.: PCT/US2008/003379
§ 371 (c)(1),
(2), (4) Date: Dec. 7, 2009

(87) PCT Pub. No.: WO2008/115411
PCT Pub. Date: Sep. 25, 2008

(65) Prior Publication Data
US 2010/0092451 A1 Apr. 15, 2010

Related U.S. Application Data

(60) Provisional application No. 60/918,432, filed on Mar. 16, 2007.

(51) Int. Cl.
*A61K 38/48* (2006.01)
*C12N 9/50* (2006.01)
*C12N 9/52* (2006.01)
*C12P 1/00* (2006.01)
*C12S 3/00* (2006.01)

(52) U.S. Cl.
USPC ......... 424/94.63; 435/219; 435/220; 435/267

(58) Field of Classification Search
None
See application file for complete search history.

(56) References Cited

U.S. PATENT DOCUMENTS

| | | | |
|---|---|---|---|
| 4,203,967 A | 5/1980 | Gallo-Torres | |
| 4,656,253 A | 4/1987 | Lewicki | |
| 4,912,120 A | 3/1990 | Castelhano et al. | |
| 4,929,630 A | 5/1990 | Castelhano et al. | |
| 5,208,021 A | 5/1993 | Johnson et al. | |
| 5,372,933 A | 12/1994 | Zamarron et al. | |
| 5,663,304 A | 9/1997 | Builder et al. | |
| 5,716,794 A | 2/1998 | Tjota | |
| 5,766,897 A | 6/1998 | Braxton | |
| 5,789,180 A | 8/1998 | Bernardin | |
| 5,811,098 A | 9/1998 | Plowman et al. | |
| 5,817,523 A | 10/1998 | Picarelli | |
| 5,834,428 A | 11/1998 | Drucker | |
| 5,912,327 A | 6/1999 | Li et al. | |
| 6,165,746 A | 12/2000 | Heitzmann et al. | |
| 6,197,356 B1 | 3/2001 | Girsh | |
| 6,294,320 B1 | 9/2001 | Hruska et al. | |
| 6,319,726 B1 | 11/2001 | Schuppan et al. | |
| 6,319,756 B2 | 11/2001 | Duesman et al. | |
| 6,395,889 B1 | 5/2002 | Robison | |
| 6,410,550 B1 | 6/2002 | Coe et al. | |
| 6,492,498 B1 | 12/2002 | Vallera et al. | |
| 6,593,106 B1 | 7/2003 | Vicik | |
| 6,610,479 B1 | 8/2003 | Lundeberg et al. | |
| 6,635,462 B1 | 10/2003 | Ensor et al. | |
| 6,642,036 B2 | 11/2003 | Flint et al. | |
| 6,645,739 B2 | 11/2003 | Clark | |
| 6,667,160 B2 | 12/2003 | Fine | |
| 6,833,447 B1 | 12/2004 | Goldman et al. | |
| 6,903,246 B2 | 6/2005 | Gallie | |
| 6,962,989 B1 | 11/2005 | Pompejus et al. | |
| 7,112,660 B1 | 9/2006 | Domingues et al. | |
| 7,144,569 B1 | 12/2006 | Anderson et al. | |
| 7,202,216 B2 | 4/2007 | Sollid et al. | |
| 7,265,093 B2 | 9/2007 | Khosla et al. | |
| 7,303,871 B2 | 12/2007 | Hausch et al. | |
| 7,320,788 B2 | 1/2008 | Shan et al. | |
| 7,442,370 B2 | 10/2008 | Sah et al. | |
| 7,462,688 B2 | 12/2008 | Khosla et al. | |
| 7,521,427 B2 | 4/2009 | Powers et al. | |
| 7,534,426 B2 | 5/2009 | Piper et al. | |
| 7,579,313 B2 | 8/2009 | Khosla et al. | |
| 7,605,150 B2 | 10/2009 | Khosla et al. | |
| 7,651,848 B2 | 1/2010 | Schlegl | |
| 7,696,338 B2 | 4/2010 | Neville, Jr. et al. | |

(Continued)

FOREIGN PATENT DOCUMENTS

DE 262999 12/1988
EP 0237082 A2 9/1987

(Continued)

OTHER PUBLICATIONS

Siegel et al. "Rational Design of Combination Enzyme Therapy for Celiac Sprue" Chemistry & Biology 13, 649-658, Jun. 2006.*
"*Novosphingobium capsulatum* gene for prolyl oligopeptidase, complete cds", GenBank: AB010298.1.
Stepniak, D., et al., "Highly efficient gluten degradation with a newly identified prolyl endoprotease: implications for celiac disease," (2006) Am J Physiol Gastrointest Liver Physiol, 291:G621-G629.
Sturgess et al., "Wheat peptide challenge in coeliac disease", The Lancet (1994), 343:758-761.
Vader et al. "The Gluten Response in Children with Celiac Sprue Disease is Directed Toward Multiple Gliadin and Glutenin Peptides," Gastroenterology, 2002, pp. 1729-1737, vol. 122.
Vader et al. "The HLA-DQ2 Gene Dose Effect in Celiac Disease is Doirectly Related to the Magnitude and Breadth of Gluten-Specific T Cell Responses," PNAS, Oct. 14, 2003, pp. 12390-12395, vol. 123, No. 3.

(Continued)

*Primary Examiner* — Thane Underdahl
(74) *Attorney, Agent, or Firm* — Bozicevic, Field & Francis LLP; Pamela J. Sherwood

(57) ABSTRACT

A combination enzyme product consisting of a glutamine specific endoprotease and a prolyl endopeptidase is provided. Both enzymes are active and stable in the stomach and can therefore be administered as lyophilized powders or simple capsules/tablets. A ratio of the two enzymes is used to maximize their synergy.

18 Claims, 6 Drawing Sheets

(56) References Cited

U.S. PATENT DOCUMENTS

| | | |
|---|---|---|
| 2001/0007690 A1 | 7/2001 | Girsh |
| 2001/0036639 A1 | 11/2001 | Fine |
| 2002/0018763 A1 | 2/2002 | Zsebo et al. |
| 2002/0039599 A1 | 4/2002 | Lin et al. |
| 2002/0076834 A1 | 6/2002 | Detlef et al. |
| 2003/0215438 A1 | 11/2003 | Hausch et al. |
| 2003/0224476 A1 | 12/2003 | Chou |
| 2004/0167069 A1 | 8/2004 | Khosla et al. |
| 2004/0241664 A1 | 12/2004 | Dekker et al. |
| 2004/0265298 A1 | 12/2004 | Lin |
| 2005/0031603 A1 | 2/2005 | Hubertus de Jong et al. |
| 2005/0049064 A1 | 3/2005 | Gagne |
| 2005/0090653 A1 | 4/2005 | Klaveness et al. |
| 2005/0176932 A1 | 8/2005 | Buus et al. |
| 2005/0227920 A1 | 10/2005 | Lin |
| 2005/0244823 A1 | 11/2005 | Drijfhout et al. |
| 2005/0249719 A1 | 11/2005 | Shan et al. |
| 2006/0052308 A1 | 3/2006 | Khosla et al. |
| 2006/0178299 A1 | 8/2006 | Anderson et al. |
| 2006/0240475 A1 | 10/2006 | Khosla et al. |
| 2007/0082369 A1 | 4/2007 | Best et al. |
| 2007/0099238 A1 | 5/2007 | Sigalas et al. |
| 2008/0299108 A1 | 12/2008 | Khosla et al. |
| 2008/0311161 A1 | 12/2008 | Gass |
| 2009/0156490 A1 | 6/2009 | Khosla et al. |
| 2009/0220554 A1 | 9/2009 | Griffin et al. |
| 2009/0304754 A1 | 12/2009 | Robic |

FOREIGN PATENT DOCUMENTS

| | | |
|---|---|---|
| EP | 0905518 A1 | 3/1999 |
| IE | 1490723 | 11/1977 |
| WO | WO 9426774 A1 | 11/1994 |
| WO | WO 9610034 A2 | 4/1996 |
| WO | 99/56698 | 11/1999 |
| WO | WO 0042213 A1 | 7/2000 |
| WO | WO 0125793 A2 | 4/2001 |
| WO | 0246381 | 6/2002 |
| WO | 02/083772 | 10/2002 |
| WO | WO 03068170 A2 | 8/2003 |
| WO | WO 03096984 A2 | 11/2003 |
| WO | WO 03104273 A2 | 12/2003 |
| WO | WO 2004045392 A2 | 6/2004 |
| WO | WO 2005049064 A1 | 6/2005 |
| WO | 2005/107786 | 11/2005 |
| WO | 2008/115428 | 9/2008 |
| WO | WO 2008115411 A1 | 9/2008 |
| WO | 2010/021752 | 2/2010 |
| WO | 2010/042203 | 4/2010 |

OTHER PUBLICATIONS

Watts; et al., "Structure-activity relationship analysis of the selective inhibition of transglutaminase 2 by dihydroisoxazoles", Journal of Medicinal Chemistry (2006), 49(25):7493-7501.
Wieser "The Precipitating Factor in Coeliac Disease," Baillieres Clinical Gastroenterol, 1995, pp. 191-207, vol. 9, Issue 2.
Wieser, "Relation Between Structure an Dcoeliac Toxicity," Acta Paediatr Suppl., 1996, pp. 3-9, vol. 412.
Wruble, Milton, "Enteric Coating. I. A Laboratory Method for the Study and Control of Enteric Coatings", Journal of the American Pharmaceutical Association, Jul. 1935, XXIV(7):570-574.
Xia; et al., Equilibrium and kinetic analysis of the unusual binding behavior of a highly immunogenic gluten peptide to HLA-DQ2, Biochemistry (2005), 44(11):4442-4449.
Yoshimoto et al., "Prolyl Endopeptidase From *Flavobacterium meningosepticum*: Cloning and Sequencing of the Enzyme Gene," J. Biochem., 1991, pp. 873-878, vol. 110.
Zhang et al. "Identification of differentially expressed proteins in human glioblastoma cell lines and tumors," Glia., Apr. 15, 2003, pp. 194-208, vol. 42, Issue 2.
Hausch et al., "Intestinal digestive resistance of immunodominant gliadin peptides", Am J Physl Gastrointest Liver Physiol (2002), 283:G996-G1003.
Pliura; et al., "Irreversible inhibition of transglutaminases by sulfonium methylketones: optimization of specificity and potency with—aminoacyl spacers", Journal of Enzyme Inhibition (1992), 6(3):181-94 (abstract).
Rohloff; et al., "Bromonitrile oxide [3+2] cycloadditions in water", Tetrahedron Letters (1992), 33(22):3113-16 (abstract).
O'Farrelly; et al., "(alpha) Gliadin antibody levels: a serological test for coeliac disease", Clinical Research (Jun. 1983), 286:2007-2010.
Hadjivassiliou; et al., "Autoantibody targeting of brain and intestinal transglutaminase in gluten ataxia", Neurology (Feb. 2006), 66:373-377.
Hadjivassiliou; et al., "Neuropathy associated with gluten sensitivity", J. Neurol. Neurosurg. Psychiatry (Jul. 2006), 77:1262-1266.
Maki; et al., "Coeliac disease", Lancet (Jun. 1997), 349:1755-1759.
Di Cagno; et al., "Proteolysis by Sourdough Lactic Acid Bacteria: Effects on Wheat Flour Protein Fractions and Gliadin Peptides Involved in Human Cereal Intolerance", Applied and Environmental Microbiology (Feb. 2002), 68(2):623-633.
Kleinbaum; et al., "New Views on Influencing Celiac Disease by Dietary Measures", International Meeting on Problems on Cereal Processing and Cereal Chemistry (1975), 7:75-83.
Krainick; et al., "Further Studies on the Harmful Effects of Wheat Flour in Celiac Disease, 2. The effect of the enzymatic degradation products of gliadin", Helvetica Paediatrica Acta (Feb. 1959), 9:124-140.
Simpson, "Proteolytic degradation of cereal prolamins—the problems with proline", Plant Science (2001), 161:825-838.
Gass; et al., "Combination Enzyme Therapy for Gastric Digestion of Dietary Gluten in Patients with Celiac Sprue", Gastroenterology (Aug. 2007), 133(2):472-480.
Ahnen et al., "Intestinal aminooligopeptidase. In vivo synthesis on intracellular membranes of rat jejunum," J. Biol. Chem., 1982, pp. 12129-12135, vol. 257.
Arentz-Hansen et al. "Celiac Lesion T Cells Recognizes Epitopes that Cluster in Regions of Gliadins Rich in Proline Residues," Gastroenterology, 2002, pp. 803-809, vol. 123, No. 3.
Arentz-Hansen et al., "The Intestinal T Cell Response to a-Gliadin in Adult Celiac Disease Is Focused on a Single Deamidated Glutamine Targeted by Tissue Transglutaminase," J. Exp. Med., 2000, pp. 603-612, vol. 191.
Arentz-Hansen, et al. (2000) "Production of a Panel of Recombinant Gliadins for the Characterisation of T Cell Reactivity in Coeliac Disease," Gut. 46(1):46-51, 2000.
Auger; et al., "Solid-State 13C NMR Study of a Transglutaminase-Inhibitor Adduct", Biochemistry (1993), 32:3930-3934.
Bethune, et al. "Heterologous expression, purification, refolding, and structural-functionalcharacterization of EP-B2, a self-activating barley cysteine endoprotease," (2006) Chemistry & Biology, 13:637-647.
Bordusa et al., "The Specificity of Prolyl Endopeptidase From Flavobacterium Meningoseptum: Mapping the S' Subsites by Positional Scanning Via Acyl Transfer," Bioorg. Med. Chem., 1998, pp. 1775-1780, vol. 6.
Campbell Monoclonal Antibody Technology Section 1.3.4, pp. 1-32, (1984) Elsvier Science Publishers.
Castelhano et al., "Synthesis, Chemistry, and Absolute Configuratin of Novel Transglutaminiase Inhibitors Containing a 3-Halo-4,5-dihydroisoxazole," Bioorg. Chem., 1988, pp. 335-340, vol. 16.
Choi et al. "Chemistry and Biology of Dihydroisoxazole Derivatives: Selectives Inhibitors of Human Transglutaminase 2," Chem. & Biol., 2005, pp. 469-475, vol. 12.
Colot et al. "The Genes Encoding Wheat Storage Proteins: Towards a Molecular Understanding of Bread-Making Quality and Its Genetic Manipulation," Genet Eng, 1990, pp. 225-241, vol. 12.
Cornell; et al., "In vitro mucosal digestion of synthetic gliadin-derived peptides in celiac disease", Journal of Protein Chemistry (1995), 14(5):335-339.
Database Derwent, Acc-No. 1996-329479, JP-08151396A, "HLA-binding oligopeptide and an immuno: regulator contg, it-used in the treatment of auto: immune diseases," Abstract, Jun. 11, 1996.
de Ritis G. et al. "In Vitro (organ culture) Studies of the Toxicity of Specific A-Gliadin Peptides in celiac Disease," Gastroenbterology, 1988, pp. 41-49, vol. 94.

(56) References Cited

OTHER PUBLICATIONS

Frazer et al. "Gluten-induced enteropathy: the effect of partially digested gluten," Lancet, Sep. 5, 1959, pp. 252-255, vol. 2.
Freund, K., et al. "Transglutaminase Inhibition by 2-[(2-Oxopropyl)thio]imidazolium Derivatives: Mechanism of Factor XIIIa Inactivation," 1994 Biochemistry 33:10109-10119.
Garcia-Maroto, et al. (1990) "Nucleotide Sequence of a cDNA Encoding an Alpha/Beta-Type Gliadin from Hexaploid Wheat (Triticum Aestivum)," Plant Molecular Biol. 14(5):867-868.
Gass et al., "Effect of Barley Endoprotease EP-B2 on Gluten Digestion in the Intact Rat", The Journal of Pharmacology and Experimental Therapeutics (2006), vol. 318, No. 3, pp. 1178-1186.
Goldsmith; et al., "Inhibition of Human Epidermal Transglutaminases In-Vitro and In-Vivo by Tyrosineamidomethyldihydrohaloisoxazoles", Journal of Investigative Dermatology (1991), 97(1):156-158.
Greenberg, C. et al. "Transglutaminases: multifunctional cross-linking enzymes that stabilize tissues," FASEB J., 1991, pp. 3071-3077, vol. 5.
Hartmann, G., et al., "Rapid degradation of gliadin peptides toxic for coeliac disease patients by proteases from germinating cereals," (2006) 44368-371.
Hausch et al. "Design, synthesis, and evaluation of gluten peptide analogs as selective inhibitors of human tissue transglutaminase," Chem Biol., Mar. 2003, pp. 225-231, vol. 10, Issue 3.
Hitomi, K., et al. "GTP, an Inhibitor of Transglutaminases, is Hydrolyzed by Tissue-Type Transglutaminase (Tgase 2) but Not by Epidermal-Type Transglutaminase (TGase 3)," Biosci. Biotechnol Biochem. 2000 pp. 657-659 vol. 64 Issue 3.
Kao Castle Pty Ltd Sequence Analysis Report by biokao Pty Ltd., PCTUS0304743, 12 pages.
Karpuj et al. "Prolonged survival and decreased abnormal movements in transgenic model of Huntington disease, with administration of the transglutaminase inhibitor cystamine," Nature Med., Feb. 2002, pp. 143-149, vol. 8, Issue 2.
Keillor, J. "Tissue Transglutaminase Inhibition," Chem. & Biol., 2005, pp. 410-412, vol. 12.
Killackey; et al., "A New Class of Mechanism-Based Inhibitors of Translutaminase Enzymes Inhibits the Formation of Cross-Linked Envelopes by Human Malignant Keratinocytes", Molecular Pharmacology (1989), 35(5):701-706.
Kim et al. "Transglutaminases in disease," Neurochem. Int, 2002, pp. 85-103, vol. 40.
Lahteenoja et al. "Local challenge on oral mucosa with an alpha-gliadin related synthetic peptide in patients with celiac disease," Am. J. Gastroenterol., 2000, pp. 2880, vol. 95.
Lion. *Flavobacterium meningosepticum.* Genbank Accession #/EMBL #: D10980. Aug. 1, 1992. http://www.infobiogen.fr/srs71bin/cgi-bin/wgeh?-id+4jqa61Mc9PO+[uniprot-ID:PPCE_FLAME]+-e, 3pgs.
Lorand et al. "Novel inhibitors against the transglutaminase-catalysed crosslinking of lens proteins," Exp Eye Res., May 1998, pp. 531-536, vol. 66.
Martinet et al. "In vivo transglutaminase type 1 expression in normal lung, preinvasive bronchial lesions, and lung cancer," Am J Respir Cell Mol Biol., Apr. 2003, pp. 428-435, vol. 28, Issue 4.

Messer et al. "Studies on the Mechanism of Destruction of the Toxic Action of Wheat Gluten in Coeliac Disease by Crude Papain," Gut., Aug. 1964, pp. 295-303, vol. 5.papain, Gut, 1964, 5:295-303.
Messer et al."Oral papain in gluten intolerance," Lancet, Nov. 6, 1976, p. 1022, vol. 2, Issue 7993.
Moodie, P. "Traditional Baking Enzymes-Proteases," Presented at the American Institute of Baking, Manhattan, Kansas, May 7, 2001 by Peter Moodie, Director—Sales & Marketing, Enzyme Development Corporation, Enzyme Development Corporation, 10pgs.
Nägele, et al. (1991) "[Analysis of Food and Feed by Partial Sequences of Characteristic Protein Components (Carrier Peptides). 1. Isolation and Structural Determination of Wheat-Specific Peptides from Chymotryptic Hydrolysates of Gliadin]," 192(5):415-421.
Online-Medical Dictionary. "Amino acid". Http://cancerweb.ncl.ac.uk./cgi-bin/omd?query=amino+acid. Nov. 13, 1997, 1 pg.
Parrot; et al., "Circular dichroism and nuclear magnetic resonance spectroscopic analysis of immunogenic gluten peptides and their analogs", Journal of Biological Chemistry (2002), 277(47):45572-45578.
Piper et al., "High selectivity of human tissue transglutaminase for immunoactive gliadin peptides: implications for celiac spure", Biochemistry, Jan. 8, 2002, pp. 386-393, vol. 41, Issue 1.
Piper, J., et al., "Effect of prolyl endopeptidase on digestive-resistant gliadin peptide in vivo," (2004) The Journal of Pharmacology and Experimental Therapeutics, 311(1):213-219.
Qiao; et al., "Antigen presentation to celiac lesion-derived T cells of a 33-mer gliadin peptide naturally formed by gastrointestinal digestion", Journal of Immunology (2004), 173(3):1757-1762.
Rudolph, R. et al., "In vitro refolding of inclusion body proteins", The FASEB Journal (Jan. 1996), vol. 10, pp. 49-56.
Sárdy, M. et al. "Epidermal transglutaminase (TGase 3) is the autoantigen of dermatitis herpetiformis," J. Exp. Med., 2002, pp. 747-757, vol. 195, Issue 6.
Schuppan et al. "Special Reports and Reviews: Current Concepts of Celiac Disease Pathogenesis," Gastroenterology, 2000, pp. 234-242, vol. 119.
Schuppan; et al., "A Molecular Warhead and its Target Tissue Transglutaminase and Celiac Sprue", Chemistry & Biology (2003), 10(3):199-201.
Shan, L. et al. "Structural Basis for Gluten Intolerance in Celiac Sprue," Science 2002, pp. 2275-2279, vol. 297.
Shan, L. et al. "Comparative biochemical analysis of three bacterial prolyl endopeptidases: implications of coeliac sprue," Biochem J, 2004, pp. 311-318, vol. 383.
Siegel; et al., "Transglutaminase 2 inhibitors and their therapeutic role in disease states", Pharmacology & Therapeutics (2007), 115:232-245.
Sjostrom et al. "Identification of a Gliadin T-Cell Epitope in Coeliac Disease: General Importance of Gliadin Deamidation for Intestinal T-Cell Recognition," Scandinavian Journal of Immunology, Aug. 1998 , pp. 111-115(5), vol. 48, No. 2.
Smith; et al., "Abnormal expression of dipeptidylpeptidase IV activity in enterocyte brush-border membranes of children suffering from coeliac disease", Experimental Physiology, Jul. 1990, 75(4):613-616.

\* cited by examiner

COMBINATION ENZYME THERAPY FOR DIGESTION OF DIETARY GLUTEN

FEDERALLY SPONSORED RESEARCH AND DEVELOPMENT

This invention was made with Government support under contract DK063158 awarded by the National Institutes of Health. The Government has certain rights in this invention.

BACKGROUND OF THE INVENTION

In 1953, it was first recognized that ingestion of gluten, a common dietary protein present in wheat, barley and rye causes a disease, now called Celiac sprue, in sensitive individuals. Gluten is a complex mixture of glutamine- and proline-rich glutenin and prolamine molecules, that appears to be responsible for disease induction. Ingestion of such proteins by sensitive individuals produces flattening of the normally luxurious, rug-like, epithelial lining of the small intestine known to be responsible for efficient and extensive terminal digestion of peptides and other nutrients. Clinical symptoms of Celiac sprue include fatigue, chronic diarrhea, malabsorption of nutrients, weight loss, abdominal distension, anemia, as well as a substantially enhanced risk for the development of osteoporosis and intestinal malignancies (lymphoma and carcinoma). The disease has an incidence of approximately 1 in 200 in European populations.

A related disease is dermatitis herpetiformis, which is a chronic eruption of the skin characterized by clusters of intensely pruritic vesicles, papules, and urticaria-like lesions. IgA deposits occur in almost all normal-appearing and perilesional skin of individuals with the disease. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine and colchicines are sometimes prescribed for relief of itching.

Celiac sprue is generally considered to be an autoimmune disease, and the antibodies found in the serum of patients support a theory of an immunological nature of the disease. Antibodies to tissue transglutaminase (tTG) and gliadin appear in almost 100% of the patients with active Celiac sprue, and the presence of such antibodies, particularly of the IgA class, has been used in diagnosis of the disease.

The large majority of patients express the HLA-DQ2 [DQ (a1*0501, b1*02)] and/or DQ8 [DQ(a1*0301, b1*0302)] molecules. It is believed that intestinal damage is caused by interactions between specific gliadin oligopeptides and the HLA-DQ2 or DQ8 antigen, which in turn induce proliferation of T lymphocytes in the sub-epithelial layers. T helper 1 cells and cytokines apparently play a major role in a local inflammatory process leading to villus atrophy of the small intestine.

At the present time, there is no approved drug therapy for the disease, and the only "treatment" is to advise patients to avoid all foods containing gluten. Although gluten withdrawal has transformed the prognosis for children and substantially improved it for adults, some people still die of the disease, mainly adults who had severe disease at the time of diagnosis. An important cause of death is lymphoreticular disease (especially intestinal lymphoma). It is not known whether a gluten-free diet diminishes this risk. Apparent clinical remission is often associated with histologic relapse that is detected only by review biopsies or by increased EMA titers.

Gluten is so widely used, for example in commercial soups, sauces, ice creams, hot dogs, and other foods, that patients need detailed lists of foodstuffs to avoid and expert advice from a dietitian familiar with celiac disease (as Celiac sprue is sometimes called). Ingesting even small amounts of gluten may prevent remission or induce relapse. Supplementary vitamins, minerals, and hematinics may also be required, depending on deficiency. A few patients respond poorly or not at all to gluten withdrawal, either because the diagnosis is incorrect or because the disease is refractory. In the latter case, oral corticosteroids (e.g., prednisone 10 to 20 mg bid) may induce response.

In view of the serious and widespread nature of Celiac sprue, improved methods of treating or ameliorating the effects of the disease are needed. Recently, a promising new approach to the treatment of the disease has been described: the use of orally ingested proteases that degrade gluten before it can exert its toxic effects in Celiac sprue and dermatitis herpetiformis patients (see U.S. Pat. Nos. 7,303,871 and 7,320,788, each of which is incorporated herein by reference). To increase the efficacy of this approach, new protease preparations with increased ability to degrade gluten, relative to currently available protease preparations, are needed. The present invention addresses such needs.

SUMMARY OF THE INVENTION

The present invention provides methods for treating the symptoms of Celiac sprue and/or dermatitis herpetiformis by decreasing the levels of toxic gluten oligopeptides in foodstuffs, either prior to or after ingestion by a patient. A combination enzyme product, consisting of a glutamine specific endoprotease (EP-B2 from barley) and a prolyl endopeptidase (SC-PEP from *Sphingomonas capsulata*) is provided. Both enzymes are active and sufficiently stable in the stomach, and can therefore be administered as lyophilized powders or simple capsules/tablets, i.e. lacking enteric coatings. The two enzymes act synergistically to degrade gluten into peptides and amino acids that are non-toxic to Celiac sprue and dermatitis herpetiformis patients. The invention provides ratios of the two enzymes that can be used to maximize their synergy using the least amount of each protease necessary to achieve that synergy.

The invention provides compositions and methods for the administration of formulations of these enzymes, as well as unit dose forms of the formulations suitable for administration to patients. Such formulations may include formulations in which the glutenase is contained within an enteric coating that allows delivery of the active agent to the intestine and formulations in which the active agents are stabilized to resist digestion in acidic stomach conditions. In another aspect of the invention, stabilized forms of the enzymes are administered to the patient, which stabilized forms are resistant to digestion in the stomach, e.g. to acidic conditions. In one aspect of the invention, a foodstuff is treated with these enzymes prior to consumption by the patient. In another aspect of the invention, the enzymes are orally administered to a patient and act internally to destroy the toxic gluten oligopeptides.

These and other aspects and embodiments of the invention are described in more detail below.

DETAILED DESCRIPTION OF THE EMBODIMENTS

Figure 1:
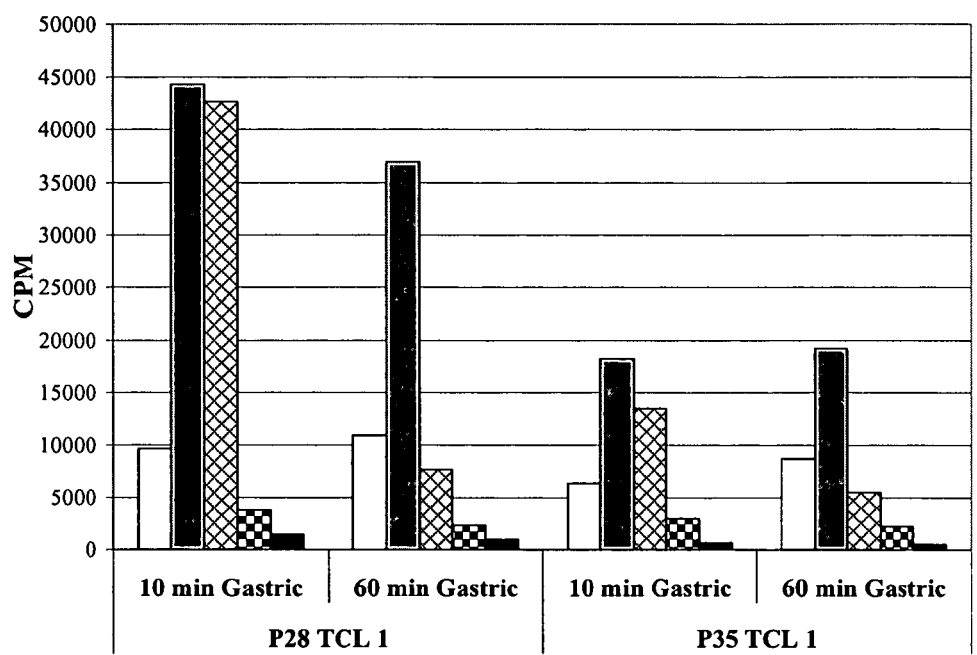
FIG. 1: Immuno-detoxification of gluten in whole wheat bread using EP-B2 as a single agent versus the combination glutenase comprised of EP-B2+SC PEP. The protein in whole wheat bread was digested under the following simulated gastric conditions: (1) pepsin (clear); (2) pepsin with 30 units EP-B2 per mg bread protein (grey shaded); (3) pepsin with 30 units EP-B2 and 0.5 mg SC PEP per mg protein (diagonal cross); (4) pepsin with 200 units EP-B2 per mg protein (checkerboard); (5) pepsin with 200 units EP-B2 and 0.5 units SC PEP per mg protein (black shaded). All digests were for 60 min at 37° C. as described below. The antigen content of samples drawn at 10 and 60 min was measured using two gluten-responsive polyclonal T cell lines (P28 TCL1 and P35 TCL 1) derived from small intestinal biopsies of unrelated Celiac sprue patients. VAVY cells were used as HLA-DQ2 homozygous antigen presenting cells. The proliferative counts per minute (CPM) were adjusted by subtracting the CPM of VAVY cells alone.

Among major dietary proteins, gluten is unique in that it contains approximately 15% proline and 35% glutamine residues. The high proline and glutamine content prevents thorough proteolysis by gastric and pancreatic enzymes, resulting in the build-up of long oligopeptides in the small intestine that are toxic to Celiac sprue and dermatitis herpetiformis patients. Proline- and glutamine-specific endoproteases, often referred to as glutenases, have been shown to be useful as therapeutic agents for Celiac sprue and dermatitis herpetiformis on account of their ability to detoxify proteolytically resistant gluten epitopes.

A new combination therapy is provided herein, consisting of a gastrically active, glutamine-specific endoprotease (EP-B2, a cysteine endoprotease from germinating barley seeds) and a duodenally active, proline-specific endopeptidase (prolyl endopeptidase; PEP), the combination of which is shown to detoxify gluten rapidly under simulated gastrointestinal conditions. By virtue of their complementary specificity for glutamine and proline residues, respectively, these two enzymes detoxify gluten more rapidly and thoroughly than either individual enzyme alone, providing a synergistic combination relative to the activity of either enzyme administered alone; particularly relative to the PEP activity. Although PEP enzymes alone have activity on intact gluten proteins, they recognize the proline-rich peptidic products of EP B2 action, and rapidly degrade residual immunotoxic epitopes.

In some embodiments, the combination of enzymes is EP-B2, which may be provided in a proenzyme form, and *Sphingomonas capsulata* PEP (SC-PEP). The present invention provides formulations in which the ratio of the two enzymes is optimized for synergism of activity. An important benefit of the EP-B2 and SC-PEP combination is that both enzymes are active over the range of pH values (pH 3-6) typically encountered in the post prandial stomach.

Gluten detoxification for a gluten sensitive individual can commence as soon as food enters the stomach, because the acidic environment (~pH 2) of the stomach favors gluten solubilization. Introduction of an acid-stable PEP or glutamine-specific protease into the stomach will synergize with the action of pepsin, leading to accelerated destruction of toxic peptides upon entry of gluten in the small intestines of Celiac sprue and/or dermatitis herpetiformis patients.

As used herein, the term "glutenase" refers to an enzyme useful in the methods and compositions of the present invention that is capable, alone or in combination with endogenous or exogenously added enzymes, of cleaving toxic (to Celiac sprue and/or dermatitis herpetiformis patients) oligopeptides of gluten proteins of wheat, barley, oats and rye into non-toxic fragments. Gluten is the protein fraction in cereal dough, which can be subdivided into glutenins and prolamines, which are subclassified as gliadins, secalins, hordeins, and avenins from wheat, rye, barley and oat, respectively. For further discussion of gluten proteins, see the review by Wieser (1996) Acta Paediatr Suppl. 412:3-9, incorporated herein by reference.

The terms "protease" or "peptidase" can refer to a glutenase and as used herein describe a protein or fragment thereof with the capability of cleaving peptide bonds, where the scissile peptide bond may either be terminal or internal in oligopeptides or larger proteins. In various embodiments, the protease or peptidase enzyme is gastrically active. Prolyl-specific peptidases and cysteine endoproteases are glutenases useful in the practice of the present invention. Each of the proteases described herein can be engineered to improve desired properties such as enhanced specificity toward toxic gliadin sequences, improved tolerance for longer substrates, acid stability, pepsin resistance, resistance to proteolysis by the pancreatic enzymes and improved shelf-life. The desired property can be engineered via standard protein engineering methods. Further descriptions of glutenases may be found, inter alia, in U.S. Pat. Nos. 7,265,093; 7,303,871; 7,202,216; and 7,320,788, each specifically incorporated by reference herein.

The amino acid sequence of a glutenase, e.g. *Sphingomonas capsulata* PEP or *Hordeum vulgare* endoprotease, can be altered in various ways known in the art to generate targeted changes in sequence and variant enzymes useful in the formulations and compositions of the invention. Such variants will typically be functionally-preserved variants, which differ, usually in sequence, from the corresponding native or parent protein but still retain the desired biological activity of cleaving gluten into non-toxic peptides and amino acids. Variants also include fragments of a glutenase that retain enzymatic activity. Various methods known in the art can be used to generate targeted changes, e.g. phage display in combination with random and targeted mutations, introduction of scanning mutations, and the like.

A variant can be substantially similar to a native sequence, i.e. differing by at least one amino acid, and can differ by at least two but usually not more than about ten amino acids (the number of differences depending on the size of the native sequence). The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); and (phenylalanine, tyrosine).

Enzyme fragments of interest include fragments of at least about 20 contiguous amino acids, more usually at least about 50 contiguous amino acids, and may comprise 100 or more amino acids, up to the complete protein, and may extend further to comprise additional sequences. In each case, the key criterion is whether the fragment retains the ability to digest the toxic oligopeptides that contribute to the symptoms of Celiac sprue into amino acids and peptides non-toxic to Celiac sprue patients.

Enzyme modifications of interest that do not alter primary sequence include chemical derivatization of proteins, e.g., acetylation or carboxylation. Also included are modifications of glycosylation, e.g. those made by modifying the glycosylation patterns of a protein during its synthesis and processing or in further processing steps; e.g. by exposing the protein to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

Also useful in the practice of the present invention are proteins that have been modified using molecular biological techniques and/or chemistry so as to improve their resistance to proteolytic degradation and/or to acidic conditions such as those found in the stomach, and to optimize solubility properties or to render them more suitable as a therapeutic agent. For example, the backbone of the peptidase can be cyclized to enhance stability (see Friedler et al. (2000) *J. Biol. Chem.* 275:23783-23789). Analogs of such proteins include those containing residues other than naturally occurring L-amino acids, e.g. D-amino acids or non-naturally occurring synthetic amino acids.

The glutenase proteins of the present invention may be prepared by in vitro synthesis, using conventional methods as known in the art. Various commercial synthetic apparatuses are available, for example, automated synthesizers by Applied Biosystems, Inc., Foster City, Calif., Beckman, and other manufacturers. If desired, various groups can be introduced into the protein during synthesis that allow for linking to other molecules or to a surface. For example, cysteines can be used to make thioethers, histidines can be used for linking to a metal ion complex, carboxyl groups can be used for forming amides or esters, amino groups can be used for forming amides, and the like.

The glutenase proteins useful in the practice of the present invention may also be isolated and purified in accordance with conventional methods from recombinant production systems and from natural sources. Protease production can be achieved using established host-vector systems in organisms such as *E. coli, S. cerevisiae, P. pastoris, Lactobacilli, Bacilli* and *Aspergilli*. Integrative or self-replicative vectors may be used for this purpose. In some of these hosts, the protease is expressed as an intracellular protein and subsequently purified, whereas in other hosts the enzyme is secreted into the extracellular medium. Purification of the protein can be performed by a combination of ion exchange chromatography, Ni-affinity chromatography (or some alternative chromatographic procedure), hydrophobic interaction chromatography, and/or other purification techniques. Typically, the compositions used in the practice of the invention will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages are based upon total protein.

One combination product of the invention comprises an effective dose of EP B2 and a PEP. In one embodiment, the EP-B2 component comprises proEP-B2, which is a proenzyme form of cysteine endoprotease B, isoform 2 (EP B2), which naturally occurs in *Hordeum vulgare* (barley). If the EP-B2 is delivered as a proenzyme, upon delivery into the acidic environment of the stomach, it rapidly self-activates into the mature enzyme (EP-B2), and efficiently proteolyses intact gluten proteins into oligopeptides. As used herein, the term "EP-B2" may refer to the mature form, the proenzyme form, or modified variants as described here, unless otherwise specified. The use of EP-B2 provides advantages, including: (i) gluten can be fully detoxified before its arrival in an affected organ or before it can induce an autoimmune response; (ii) it does not require formulation via enteric coating; and (iii) enzyme stability in the presence of bile acids is not a major concern. If the EP-B2 is delivered as a proenzyme, upon delivery into the acidic environment of the stomach, it rapidly self-activates into the mature enzyme (EP-B2), and efficiently proteolyses intact gluten proteins into oligopeptides.

In some embodiments, the proEP-B2 is further engineered to delete the native signal sequence, which allows for high expression of proEP-B2 as inclusion bodies in *E. coli*. Optionally the sequence further comprises affinity tags to facilitate purification, e.g. N-terminal and/or C-terminal hexa-histidine tags, which have high affinity for commercially available nickel affinity resins. An example of a suitable proEP-B2 proenzyme sequence is provided in SEQ ID NO:1. An example of a suitable native EP-B2 proenzyme is provided in SEQ ID NO:3; and the sequence of the corresponding mature enzyme, which may also find use in the compositions of the invention, is provided as SEQ ID NO:4.

The specific activity of proEP-B2 is defined by the activity of the mature enzyme form, where 1 unit is defined as 1 µM p-nitroaniline released per minute from a chromogenic substrate CBz-Phe-Arg-pNA at room temperature. Enzyme formulation may be provided where the specific activity is at least about 500 U/mg, at least about 1000 U/mg, or higher.

PEPs belong to the serine protease superfamily of enzymes and have a conserved catalytic triad composed of a Ser, His, and Asp residues, and include enzymes from *F. meningosepticum, Aeromonas hydrophila, Aeromonas punctata, Novosphingobium capsulatum, Pyrococcus furiosus, Aspergillus niger*, and from mammalian sources are biochemically characterized PEPs. Specific PEP enzymes of interest include, without limitation, *Flavobacterium meningosepticum* PEP (Genbank ID # D10980); *Myxococcus xanthus* PEP (Genbank ID# AF127082); *Sphingomonas capsulata* PEP (Genbank ID# AB010298); *Lactobacillus helveticus* PEP (Genbank ID#321529); and *Penicillium citrinum* PEP (Genbank ID# D25535).

In one embodiment of the invention, the PEP is *Sphingomonas capsulata* PEP (SC PEP). In some embodiments, the genetic sequence is altered from the native sequence to utilize codons optimized for high expression as a soluble cytosolic protein in *E. coll*. Optionally the sequence further comprises affinity tags to facilitate purification, e.g. N-terminal and/or C-terminal hexa-histidine tags, which have high affinity for commercially available nickel affinity resins. An example of a suitable SC-PEP sequence is provided in SEQ ID NO:2. An example of a suitable native SC-PEP sequence is provided in SEQ ID NO:5.

The specific activity of SC-PEP is defined by the activity of the mature enzyme form, where 1 unit is defined as 1 µM p-nitroaniline released per minute from a chromogenic substrate (Cbz-Gly-Pro-pNA) at room temperature. Enzyme formulation can be provided where the specific activity is at least about 500 U/mg, at least about 1000 U/mg, or higher.

A combination drug product of the invention can be defined based on the activity units of the two enzymes per dosage unit. On an activity basis, the ratio of EP-B2:PEP is usually from about 10:1 to about 1:10; from about 5:1 to about 1:5; from about 5:1 to about 1:1; from about 5:1 to about 2:1; and in some embodiments is about 4:1; about 5:3; about 5:2; or about 3:1.

To demonstrate the synergistic activity of the two enzymes and to establish an appropriate fixed-dose ratio for clinical investigation, varying amounts of proEP-B2 and PEP have been added to whole wheat bread under simulated gastric conditions (i.e., 1 g bread incubated for 10-60 minutes at 37° C. with 6.67 ml 0.01 N HCl containing 0.6 mg/mL pepsin and an appropriate amount of enzymes). Samples are analyzed by reverse-phase HPLC under conditions that have been optimized to resolve the entire spectrum of peptides released via gastrointestinal hydrolysis of gluten. The combination of the two enzymes was found to have a strong synergistic effect on gluten detoxification, particularly at the indicated enzyme ratios.

In one aspect, the present invention provides a unit dose form of the EP-B2:SC-PEP formulation of the invention. In one embodiment, the unit dose form contains from 100 to 1000 mg of each glutenase. In one embodiment, the unit dose form contains from 100; 300, 900, 1800, 2000 mg of total enzyme, where, for example, SC-pep may have a specific activity of about 2500 Units/mg, and proEP-B2 may have a specific activity of 4000 Units/mg, and where the ratio of enzymes is as described herein.

In one aspect, the present invention provides a purified preparation of the combined glutenases, which preparation may be provided as a bulk lyophilized powder; formulated into unit dosages; etc. The enzymes may be provided separately, or in a combined formulation. The term "unit dosage form," refers to physically discrete units suitable as unitary dosages for human subjects, each unit containing a predetermined quantity of glutenase in an amount calculated sufficient to produce the desired effect in association with a pharmaceutically acceptable diluent, carrier or vehicle. The specifications for the unit dosage forms of the present invention depend on the particular combination employed and the effect to be achieved, and the pharmacodynamics associated with the host.

In one aspect, the agents are formulated into pharmaceutical compositions by combination with appropriate, pharmaceutically acceptable carriers or diluents, and are formulated into preparations in solid, semi-solid, liquid, suspension, emulsion, or gaseous forms, such as tablets, capsules, powders, granules, ointments, solutions, suspensions, emulsions, suppositories, injections, inhalants, gels, microspheres, and aerosols. As such, administration of the glutenase and/or other compounds can be achieved in various ways, usually by oral administration. In pharmaceutical dosage forms, the glutenases may be administered in the form of their pharmaceutically acceptable salts, or they may also be used alone or in appropriate association, as well as in combination with other pharmaceutically active compounds. The following methods and excipients are exemplary and are not to be construed as limiting the invention.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Exemplary organic bases are isopropylamine, diethylamine, ethanolamine, trimethylamine, dicyclohexylamine, choline and caffeine.

Although not required, oral formulations optionally comprise enteric coatings, so that the active agent is delivered to the intestinal tract. A number of methods are available in the art for the efficient delivery of enterically coated proteins into the small intestinal lumen. Most methods rely upon protein release as a result of the sudden rise of pH when food is released from the stomach into the duodenum, or upon the action of pancreatic proteases that are secreted into the duodenum when food enters the small intestine. For intestinal delivery of a PEP and/or a glutamine specific protease, the enzyme is usually lyophilized in the presence of appropriate buffers (e.g. phosphate, histidine, imidazole) and excipients (e.g. cryoprotectants such as sucrose, lactose, trehalose). Lyophilized enzyme cakes are blended with excipients, then filled into capsules, which are enterically coated with a polymeric coating that protects the protein from the acidic environment of the stomach, as well as from the action of pepsin in the stomach. Alternatively, protein microparticles can also be coated with a protective layer. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate. Other enteric formulations comprise engineered polymer microspheres made of biologically erodable polymers, which display strong adhesive interactions with gastrointestinal mucus and cellular linings and can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) *J Control Release* 71(3):307-18.

Various methods for administration may be employed, preferably using oral administration, for example with meals. The dosage of the therapeutic formulation can vary widely, depending upon the nature of the disease, the frequency of administration, the manner of administration, the clearance of the agent from the host, and the like. The dose will typically be administered daily, with meals, or only with those meals suspected of containing gluten. In another embodiment, the glutenase is admixed with food, or used to pre-treat foodstuffs containing glutens. Glutenase present in foods can be enzymatically active prior to or during ingestion, and may be encapsulated or otherwise treated to control the timing of activity. Alternatively, the glutenase may be encapsulated to achieve a timed release after ingestion, e.g. in the intestinal tract.

The methods of the invention can be used for prophylactic as well as therapeutic purposes. As used herein, the term "treating" refers both to the prevention of disease and the treatment of a disease or a pre-existing condition. The invention provides a significant advance in the treatment of ongoing disease, to stabilize or improve the clinical symptoms of the patient. Such treatment is desirably performed prior to loss of function in the affected tissues but can also help to restore lost function or prevent further loss of function. Evidence of therapeutic effect may be any diminution in the severity of disease, particularly as measured by the severity of symptoms such as fatigue, chronic diarrhea, malabsorption of nutrients, weight loss, abdominal distension, anemia, and other symptoms of Celiac sprue and/or dermatitis herpetiformis. Other disease indicia include the presence of antibodies specific for glutens, the presence of antibodies specific for tissue transglutaminase, the presence of pro-inflammatory T cells and cytokines, damage to the villus structure of the small intestine as evidenced by histological or other examination, enhanced intestinal permeability, skin lesions, and the like.

Patients that may be treated by the methods of the invention include those diagnosed with Celiac sprue through one or more of serological tests, e.g. anti-gliadin antibodies, anti-transglutaminase antibodies, anti-endomysial antibodies; endoscopic evaluation, e.g. to identify celiac lesions; histological assessment of small intestinal mucosa, e.g. to detect villous atrophy, crypt hyperplasia, infiltration of intra-epithelial lymphocytes; and any GI symptoms dependent on inclusion of gluten in the diet. Amelioration of the above symptoms upon introduction of a strict gluten-free diet is a key hallmark of the disease. However, analysis of Celiac sprue patients has shown that a high level of patients believed to be in remission are, in fact, suffering malabsorption, as evidenced by indicia including, without limitation, xylose absorption tests, fecal fat analysis, lactulose/mannitol permeability tests, and the like. In some embodiments of the invention, patients are evaluated by examination of intestinal malabsorption for initial diagnosis, assessment, and/or monitoring during and after treatment.

Given the safety of orally administered proteases, they also find a prophylactic use in high-risk populations, such as Type I diabetics, family members of diagnosed celiac patients, HLA-DQ2 positive individuals, and/or patients with gluten-associated symptoms that have not yet undergone formal diagnosis. Such patients may be treated with regular-dose or low-dose (10-50% of the regular dose) enzyme. Similarly, temporary high-dose use of such an agent is also anticipated for patients recovering from gluten-mediated enteropathy in whom gut function has not yet returned to normal, for example as judged by fecal fat excretion assays.

Patients that can benefit from the present invention may be of any age and include adults and children. Children in particular benefit from prophylactic treatment, as prevention of early exposure to toxic gluten peptides can prevent initial development of the disease. Children suitable for prophylaxis can be identified by genetic testing for predisposition, e.g. by HLA typing; by family history, by T cell assay, or by other medical means. As is known in the art, dosages may be adjusted for pediatric use.

The therapeutic effect can be measured in terms of clinical outcome or can be determined by immunological or biochemical tests. Suppression of the deleterious T-cell activity can be measured by enumeration of reactive Th1 cells, by quantitating the release of cytokines at the sites of lesions, or using other assays for the presence of autoimmune T cells known in the art. Alternatively, one can look for a reduction in symptoms of a disease.

In one embodiment of the present invention, a Celiac sprue patient is, in addition to being provided a glutenase or food treated in accordance with the present methods, provided an inhibitor of tissue transglutaminase, an anti-inflammatory agent, an anti-ulcer agent, a mast cell-stabilizing agents, and/or and an-allergy agent. Examples of such agents include HMG-CoA reductase inhibitors with anti-inflammatory properties such as compactin, lovastatin, simvastatin, pravastatin and atorvastatin; anti-allergic histamine H1 receptor antagonists such as acrivastine, cetirizine, desloratadine, ebastine, fexofenadine, levocetirizine, loratadine and mizolastine; leukotriene receptor antagonists such as montelukast and zafirlukast; COX2 inhibitors such as celecoxib and rofecoxib; p38 MAP kinase inhibitors such as BIRB-796; and mast cell stabilizing agents such as sodium chromoglycate (chromolyn), pemirolast, proxicromil, repirinast, doxantrazole, amlexanox nedocromil and probicromil.

As used herein, compounds which are "commercially available" may be obtained from commercial sources including but not limited to Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.), Novabiochem and Argonaut Technology.

Compounds can also be made by methods known to one of ordinary skill in the art. As used herein, "methods known to one of ordinary skill in the art" may be identified though various reference books and databases. Suitable reference books and treatises that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

The present invention relates generally to methods and reagents useful in treating foodstuffs containing gluten with enzymes that digest the oligopeptides toxic to Celiac sprue patients. Although specific enzymes are exemplified herein, any of a number of alternative enzymes and methods apparent to those of skill in the art upon contemplation of this disclosure are equally applicable and suitable for use in practicing the invention. The methods of the invention, as well as tests to determine their efficacy in a particular patient or application, can be carried out in accordance with the teachings herein using procedures standard in the art. Thus, the practice of the present invention may employ conventional techniques of molecular biology (including recombinant techniques), microbiology, cell biology, biochemistry and immunology within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction" (Mullis et al., eds., 1994); and "Current Protocols in Immunology" (J. E. Coligan et al., eds., 1991); as well as updated or revised editions of all of the foregoing.

The following examples are intended to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

This application specifically references U.S. Pat. Nos. 7,320,788; 7,303,871; 7,265,093; and 7,202,216, each of which is specifically incorporated herein by reference.

Example 1

Materials & Methods

Materials:

Whole wheat bread (Alvarado St Sprouted Whole Wheat Bread) was from Alvarado St Bakery (Rohnert Park, Calif.). Pepsin was obtained from American Laboratories (Omaha, Nebr.). Trypsin (from bovine pancreas, T4665), α-chymotrypsin (type II from bovine pancreas, C4129), elastase (from porcine pancreas, E7885) and carboxypeptidase A (type II from bovine pancreas, C-0386) were from Sigma (St. Louis, Mo.). Substrates for the chromogenic assays for PEP (Z-Gly-Pro-p-Nitroanilide) and EP-B2 (Z-Phe-Arg-pNA) were from Bachem (Torrance, Calif.). All materials used in the animal studies were food-grade or higher. Vancomycin was from Sigma. All other reagents were food or reagent grade.

EP-B2 and SC PEP Enzyme Manufacturing and Testing:

EP-B2 was prepared in its zymogen as described in U.S. provisional patent application Ser. No. 60/895,413, filed 16 Mar. 07; see also copending PCT patent application No. US2008/003425, filed 14 Mar. 08. SC PEP was prepared as described previously (Shan et al. Biochem J 2004; 383:311-8). EP-B2 concentration was between 5.8-15.5 mg/ml in 100 mM Tris-Cl, 5 mM EDTA, 2 mM β-mercaptoethanol, 15% sucrose, pH 8, with specific activity ranging between 800-

5000 units/mg. SC PEP was prepared in 20 mM sodium phosphate buffer, pH 7, or phosphate-buffered saline, pH 7.4, at a concentration between 60-90 mg/mL and specific activity of 15-20 units/mg. Enzyme activity assays were performed as described by Marti et al. J Pharmacol Exp Ther 2005; 312: 19-26.

In Vitro Whole Wheat Bread Digestion:

To evaluate the efficacy of alternative glutenases, an in vitro experimental protocol was developed to mimic the ingestion and digestion of whole wheat bread from a grocery store. Alvarado St Sprouted Whole Wheat Bread was selected because of its high protein level (label claim of 4 g protein for 38 g slice). A portion of a bread slice (typically 1 g) was pre-soaked with specified levels of EP-B2 and SC PEP solutions, formulated in their respective buffers. Additional EP-B2 refolding buffer (100 mM Tris-Cl, 5 mM EDTA, 2 mM β-mercaptoethanol, 15% sucrose, pH 8) was added to the bread so that 888 μL total liquid was added to 1 g bread. This additional buffer was added to allow for variation in the EP-B2 enzyme dosage. The bread was divided into 6 pieces.

To initiate the in vitro digestion protocol, the pre-soaked bread pieces were added to a 0.01 N HCl solution (pH 2, pre-incubated at 37° C.) containing 0.6 mg/mL pepsin. Approximately 6.67 mL 0.01 HCl solution was added to 1 g bread (starting weight before any liquid addition) to achieve a final protein concentration of approximately 15 mg/mL in the suspension. The bread pieces were added over 15 min (at 3 min intervals) and, after addition of each piece, the mixture was manually agitated with a spatula. The pH was approximately 4.5 at the end of the ingestion phase.

The simulated gastric digestion phase was considered to start upon addition of the last bread piece to the 0.01 N HCl solution. The material was incubated at 37° C. for various times (typically, 10 min to mimic short gastric digestion or 60 min to mimic extended gastric digestion). Samples (500 μL) were taken at 0, 10, 30, and 60 min and immediately heated at >95° C. for at least 5 min to inactivate the enzymes. The mixture was manually agitated with a spatula prior to each sampling event.

In experiments where duodenal digestion was simulated, at the end of the gastric phase, the pH was adjusted to 6.0 by the addition of sodium phosphate (15 mg for a 1 g bread digest) and 1 M HCl and/or 1 M NaOH. Pancreatic enzymes (trypsin and chymotrypsin, or trypsin, chymotrypsin, elastase, and carboxypeptidase A), prepared in ~50 mg/mL stock solutions, were added to yield the following final concentrations: 0.375 mg/mL trypsin, 0.375 mg/mL chymotrypsin, 0.075 mg/mL elastase, and 0.075 mg/mL carboxypeptidase A. The final solution was then incubated at 37° C. for up to 30 min. Samples (500-1000 μL) were withdrawn at 10 and 30 min, and heat-treated as described above.

In Vivo Whole Wheat Bread Experiments in Rats:

An existing animal experimental protocol for monitoring gluten digestion in rats was modified to evaluate the effect of EP-B2+SC PEP on whole wheat bread. Briefly, rats were acclimated to eat bread over the course of 2 days. The rats were fasted for a minimum of 12 h (maximum of 24 h) prior to the start of the experiment. They were then fed 4 g bread (starting weight) that had been pre-soaked with specified levels of EP-B2 (30 units per mg protein), EP-B2 (30 units per mg protein)+SC PEP (1.67 units per mg protein), or buffer alone (100 mM Tris-Cl, 5 mM EDTA, 2 mM β-mercaptoethanol, 15% sucrose, pH 8). The rats were allowed to eat and digest the bread meal for 120 min and were then euthanized by $CO_2$ exposure. The gastric contents of the animals were collected in a 15 mL Falcon tube and immediately frozen using a dry ice/ethanol bath. Gastric material was analyzed by removing approximately 250 mg of the frozen sample, heating the 250 mg aliquot at >95° C. for at least 10 min to inactivate all enzymes, and then centrifuging the material at 15,000 RPM for 10 min. The supernatant was collected and analyzed.

Reverse Phase HPLC:

Samples from the in vitro whole wheat bread digests or harvested from rat stomach were chromatographically separated on a 4.6×150 mm reverse phase $C_{18}$ protein and peptide column (Grace Vydac, Hesperia, Calif.) using Varian-Rainin Dynamax (Palo Alto, Calif.) SD-200 pumps (1 ml/min), a Varian 340 UV detector set at 215 nm and a Varian Prostar 430 autosampler. Solvent A was water with 5.0% acetonitrile and 0.1% trifluoroacetic acid. Solvent B was acetonitrile with 5.0% water and 0.1% trifluoroacetic acid. Prior to injection, samples were centrifuged for 10 min at approximately 14,000·g and filtered through a 0.2 μm syringe filter.

Indirect Competitive ELISA for Gliadin Peptides:

The relative amount of gliadin in each sample was determined by indirect competitive ELISA. To prepare the coating solution, 20 mg/ml gliadin (Sigma) was digested in 0.01 M HCl for 60 min at 37° C. with 0.6 mg/ml pepsin. The reaction was then adjusted to pH 6.0 with $Na_2HPO_4$ and 0.375 mg/ml trypsin was added to further digest the gliadin for 120 min at 37° C. The reaction was quenched by boiling 10 min and frozen at −20° C. until use.

On day 1 of the ELISA procedure, pepsin-trypsin digested gliadin (PT-gliadin) was diluted to 20 mg/ml in coating solution (50 mM sodium carbonate/bicarbonate buffer, pH 9.6, 0.02% $NaN_3$) and 200 ml/well was incubated overnight at 4° C. in 96-well microtiter plates (Nunc Maxisorp; Nalge Nunc International, Rochester, N.Y.). Samples were diluted 1:100-1:1,296,000 in StartingBlock T20 TBS blocking buffer (Pierce, Rockford, Ill.) and incubated overnight at 4° C. with an equal volume of 5.1 mg/ml rabbit polyclonal anti-gliadin antibody (Sigma). On day 2, antigen-coated plates were washed thrice with 1× phosphate-buffered saline, pH 7.4, 0.05% Tween-20 prior to blocking and between all subsequent steps. Plates were blocked with 200 ml/well blocking buffer for 2 h at room temperature. Antibody/sample mixes were added to the wells in triplicate (200 ml/well) and incubated overnight at 4° C. On day 3, goat anti-rabbit IgG-alkaline phosphatase conjugate (Sigma) was diluted 1:250 in blocking buffer and 200 ml/well was incubated 3 h at room temperature. Freshly prepared substrate solution (5 mg/ml pNPP, 50 mM sodium carbonate/bicarbonate buffer, pH 9.8, 1 mM $MgCl_2$, 0.02% $NaN_3$) was added (200 ml/well) and the absorbance at 405 nm was measured every 6 seconds for 5 minutes.

The initial rate ($mA_{405}$/min) in each well was determined from 31 data points. For each sample, the mean initial rate at each dilution was plotted against the corresponding dilution, yielding a hyperbolic curve. To determine the dilution required for half maximal reduction of initial rate for each sample ($IC_{50}$), the inflection point of each curve was determined using the HyperbolaGen model in the curvefitting program Origin 6.0 (OriginLab Corporation; Northampton, Mass.). Values shown are the mean±SD of two separate experiments, each run in triplicate, on separate days unless otherwise indicated.

T Cell Lines and $^3$H Thymidine T Cell Proliferation Assay.

The T cell lines P28 TCL1 and P35 TCL1 were generated and characterized as described by Siegel et al. Chem Biol 2006; 13:649-58. T cell proliferation assays were performed using DQ2 homozygous VAVY cells as described in Siegel et al. except 1 μCi/well of [methyl-$^3$H]-thymidine was pulsed for 24 hours before harvesting the cells. Samples were analyzed in duplicate and the counts per minute (CPM) were adjusted by subtracting the CPM of VAVY cells alone. Blanks represent the CPM of T cells plus VAVY cells in the absence of any gluten sample.

Results

In Vitro Digestion of Whole Wheat Bread:

To evaluate the efficacy of individual versus combination glutenase therapies, whole wheat bread was digested in vitro as per protocols detailed in the Materials and Methods section. The digests were analyzed using HPLC analysis, indirect competitive ELISA, and T cell proliferation assays. In vitro digestion of bread under simulated gastric conditions differs from that of uncooked whole gluten. In the case of whole gluten, most of the protein dissolves under simulated gastric conditions. In contrast, acid and pepsin alone are insufficient to dissolve the protein in bread, and pancreatic enzymes are required to fully solubilize the gluten protein.

EP-B2 Digestion of Whole Wheat Bread:

In a previous study, we have characterized in detail the reverse-phase HPLC profiles of whole gluten following treatment under simulated gastric and duodenal conditions (see Gass et al. Biotechnol Bioeng 2005; 92:674-84). Under these analytical conditions, most immunotoxic peptides have retention times higher than 12.5 min. For example, representative antigenic gluten oligopeptides comprised of 9, 11, 12, 14, 21 and 28 residues elute at 12.5 min, 18.5 min, 21.5 min, 22.5 min and 22 min, respectively. A small fraction of the undigested gluten protein elutes at 25 min (the remainder being tightly bound to the guard column). The relatively broad 25 min peak also includes other long gluten-derived peptides (>30 residues); for example, a highly immunogenic 33-mer peptide elutes at 25 min.

The glutenase activity of EP-B2 was evaluated at doses ranging from 10-200 units EP-B2 per mg bread protein. Low levels of EP-B2 (10 units EP-B2 per mg protein) were sufficient to dramatically change the gluten oligopeptide profile. Notably, the abundance of late eluting peaks (23-25 min) reduced considerably, whereas the area under the curve from 12-23 min increased compared to the pepsin-only control. As the EP-B2:gluten ratio was increased, the area under the curve of all peaks eluting after 12 min reduced, whereas the early eluting peaks became more abundant. Interestingly, a steady decrease in the area under the curve corresponding to the gluten oligopeptide region (12-23 min) was observed up to the highest EP-B2 dose evaluated. In contrast, complete elimination of gluten metabolites eluting at 23-25 min was achieved at EP-B2 doses higher than 30 units per mg protein, indicating that EP-B2 preferentially digests longer gluten peptides. The addition of EP-B2 also caused an increase in the amount of soluble protein present in the digest (versus the pepsin-only control).

An indirect competitive ELISA assay, using anti-gliadin antibodies for rabbits, was developed to compare the relative level of gliadin oligopeptides in the various whole wheat bread digests. The results support the HPLC analysis and demonstrate that the use of EP-B2 can decrease the level of gliadin antigens (Table 1). Interestingly, the low dose of EP-B2 (10 units per mg protein) has similar $IC_{50}$ value as the pepsin only control. A decrease in the gliadin antigen level is observed from 30-200 EP-B2 units per mg protein.

TABLE 1

Competitive ELISA results for EP-B2 ± SC PEP digestion of whole wheat bread:

| Experimental Condition | $IC_{50}$ | % of Gliadin Epitopes |
|---|---|---|
| Pepsin | 3.13E−05 (±1.25E−05) | 100.0 |
| EP-B2 (10 units) | 2.62E−05 | 119.4 |
| EP-B2 (30 units) | 5.77E−04 (±3.44E−04) | 5.4 |
| EP-B2 (100 units) | 1.52E−03 | 2.1 |
| EP-B2 (200 units) | 5.87E−03 | 0.5 |
| EP-B2 (10 units) + SC PEP (1.67 units) | 7.89E−05 | 39.6 |
| EP-B2 (30 units) + SC PEP (0.50 units) | 9.00E−04 | 3.5 |
| EP-B2 (100 units) + SC PEP (0.50 units) | 4.66E−03 | 0.7 |
| EP-B2 (200 units) + SC PEP (0.50 units) | 5.78E−03 | 0.5 |

The $IC_{50}$ values for various in vitro whole wheat bread digests are presented. All digests were performed under simulated gastric conditions for 60 min. The results are presented as average values of two experimental runs (each performed in triplicate), except for the Pepsin control and the EP-B2 (30 units) digests. For these conditions, multiple digests (n = 2 for Pepsin; n = 3 for EP-B2 (30 units)) were tested and all results were averaged (±1 SD). The "% of Gliadin Epitopes" corresponds to the abundance of epitopes (i.e. sequences recognized by the commercially available polyclonal anti-gliadin antiserum) in the sample relative to that of the pepsin control. The value is calculated by defining the gliadin epitope level in the pepsin control as 100%.

T cell proliferation assays, using two patient-derived polyclonal cell lines, were used to assess the residual gluten toxicity of selected samples from the above experiments (FIG. 1). A low dose of 30 units EP-B2 per mg protein was insufficient to detoxify gluten even after 60 min of gastric digestion. The apparent increase in immunotoxicity of EP-B2 treated bread versus the pepsin-only control is due to the inability of pepsin to proteolyze gluten in bread sufficiently so as to release peptidic antigens of suitable length for T cell presentation in this assay. At a higher dose of EP-B2 (200 units per mg protein), the residual gluten toxicity is markedly reduced. These results are comparable to previous studies on uncooked whole gluten.

Figure 2:
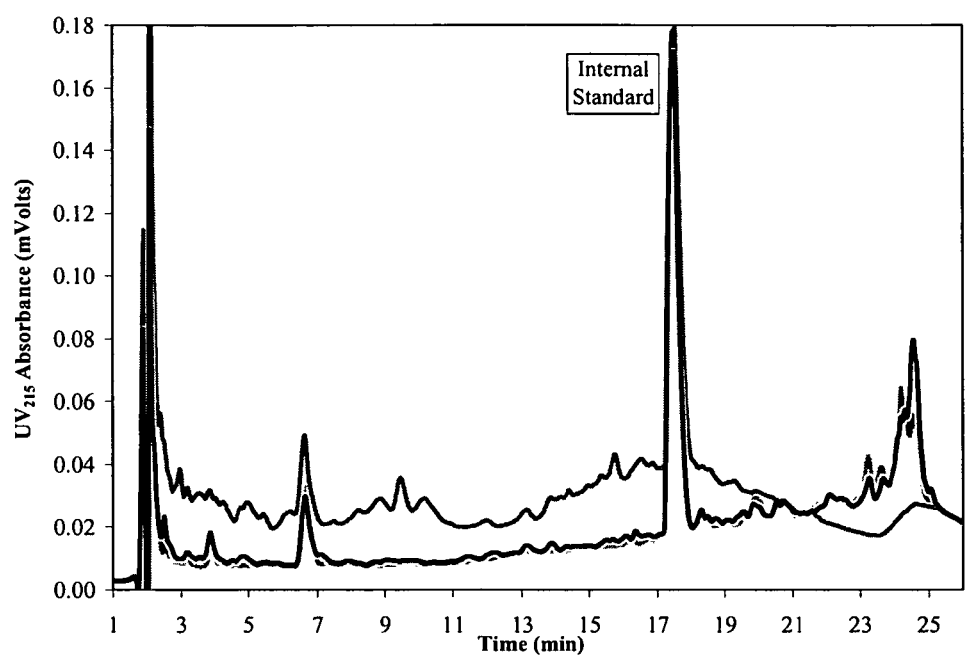
FIG. 2: Comparison of the effect of single-agent enzymes on gluten digestion in whole wheat bread. The HPLC traces represent protein whole wheat bread that has been digested in vitro with pepsin only (—) EP-B2 only (—), and pepsin with SC PEP (—). EP-B2 (30 units per mg protein), pepsin (0.6 mg/mL), and SC PEP (1.67 units per mg protein) were added prior to the start of the simulated gastric digestion. All digestions were performed for 60 min at 37° C. Standard peaks are defined in the legend to FIG. 1.

EP-B2 and SC PEP Digestion of Whole Wheat Bread:

To evaluate the synergistic potential of EP-B2 and SC PEP in the gastric environment, the combination product was compared with both individual enzymes using the in vitro bread digestion protocol described above. As summarized above, EP-B2 alone (in the absence of pepsin) efficiently breaks down full-length gluten proteins into relatively short oligopeptides, although relatively high concentrations of this enzyme are required to detoxify the gluten in whole wheat bread completely. In contrast, while SC PEP has high specificity for immunotoxic gluten oligopeptides, it has minimal ability to detoxify gluten by itself (or together with pepsin) (FIG. 2), presumably due to its relatively low specificity for long-chain substrates. Therefore, for the combination glutenase agent to be effective, EP-B2 must rapidly cleave intact gluten proteins at glutamine residues, whereas SC PEP must efficiently attack internal proline residues in the resulting oligopeptides (see FIG. 4 for an example of such synergistic action). Additionally, the two enzymes must be reasonably stable in each other's presence.

At a moderate dose ratio of 30 units EP-B2 and 0.5 units SC PEP per mg bread protein, EP-B2 did not significantly alter SC PEP stability. Approximately 40-50% of the initial SC PEP was retained after 60 min of simulated gastric digestion, independent of whether EP-B2 was present or not. The activity loss of SC PEP was due to the exposure of this enzyme to low pH conditions, as also seen earlier. Similarly, the presence of SC PEP did not affect EP-B2 activity.

Figure 3A:
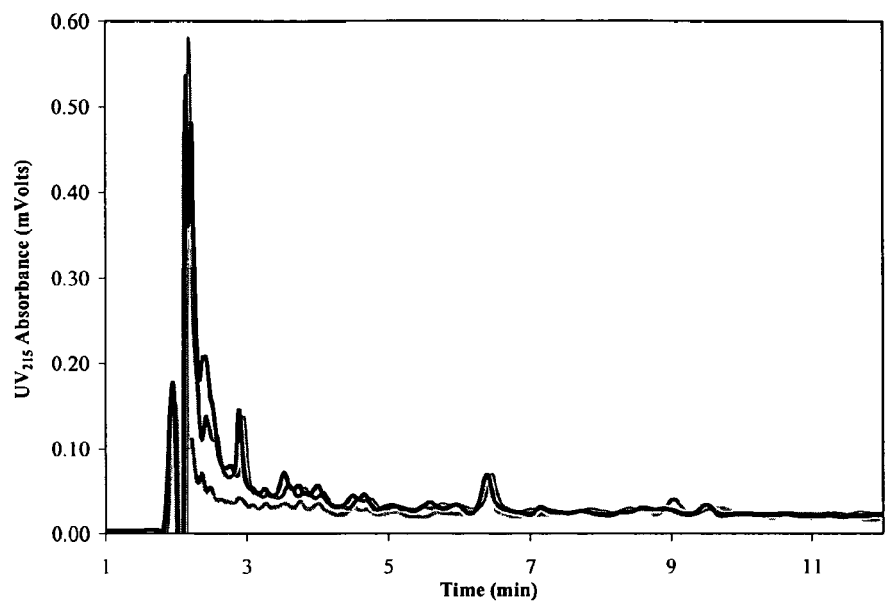
FIG. 3: Effect of EP-B2+PEP on gluten digestion in whole wheat bread. HPLC traces represent protein from whole wheat bread treated with EP-B2 only (—), EP-B2 plus FM PEP (—) and EP-B2 plus SC PEP (—). In all cases, EP-B2 (30 units per mg protein), pepsin (0.6 mg/mL), and PEP (1.67 units per mg protein) doses were used. For EP-B2 only and EP-B2+SC PEP cases, all enzymes were added at the start of the simulated gastric digestion, and the 60 min gastric results are presented. In contrast, for the EP-B2+FM PEP case, FM PEP was added after the 60 min simulated gastric digest, following pH adjustment to 6 and addition of 0.375 mg/mL trypsin and chymotrypsin. The 10 min intestinal results are presented for the EP-B2+FM PEP case. The internal HPLC standard (N-a-p-Tosyl-L-Arginine methyl ester) is labeled. Under these HPLC conditions, representative antigenic gluten oligopeptides comprised of 9, 11, 12, 14, 21 and 28 residues elute at 12.5 min, 18.5 min, 21.5 min, 22.5 min and 22 min, respectively.
Figure 3B:
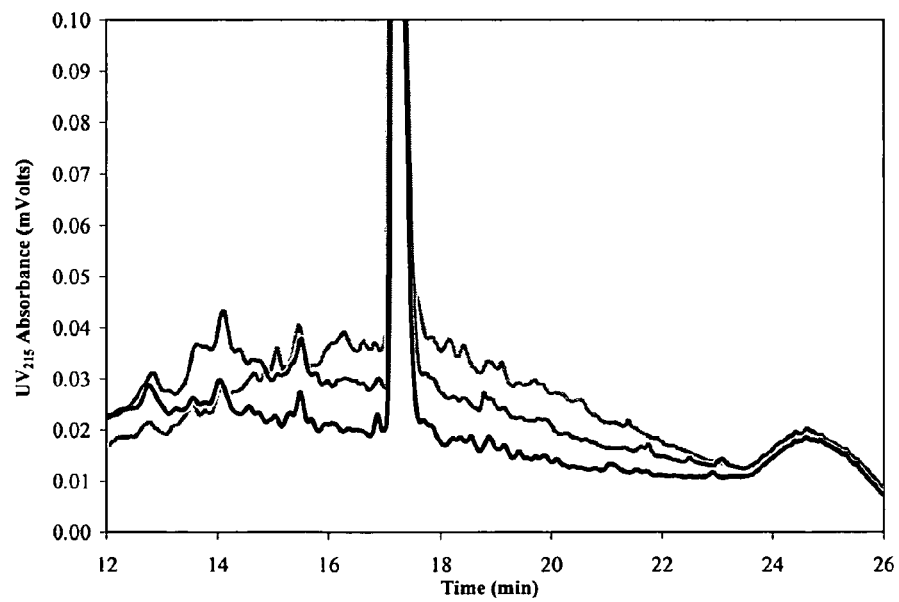

In addition to comparing the activity of EP-B2+SC PEP to each enzyme individually, this new combination product was also compared to another combination product comprised of EP-B2 (added to the gastric phase of digestion) and the FM PEP from *Flavobacterium meningosepticum* (added to the duodenal phase of digestion) (FIG. 3). The latter combination was used as a benchmark control in the present study, as it was extensively analyzed in an earlier study and shown to detoxify whole gluten thoroughly and rapidly. The HPLC results in FIGS. 3a and 3b demonstrate that SC PEP is highly effective at reducing the abundance of gluten oligopeptides (14-24 min) produced via the action of EP-B2 on wheat bread. This reduction is accompanied by a marked increase in the early eluting peaks (2-4 min), which are presumably small digestion products (i.e. di- and tri-peptides). Indeed, the simulated gastric action of the EP-B2+SC PEP combination on whole wheat bread appears to be at least as thorough as the simulated gastric plus duodenal action of EP-B2+FM PEP combination. This comparison is noteworthy because the latter treatment also includes the action of pancreatic enzymes, whereas the former treatment does not.

Identifying the Optimal Dose Ratio of EP-82 and SC PEP:

To evaluate a combination glutenase in clinical trials efficiently, a fixed dose ratio of the two active ingredients must be specified. To determine this optimal dose ratio, different amounts of SC PEP, ranging from 0.17-1.67 units per mg gluten protein, were combined with EP-B2 doses of 10 and 200 units per mg protein (FIG. 4). Enzyme manufacturing processes for EB-B2 and SC PEP described herein routinely yield enzymes with specific activities >3500 units/mg and >30 units/mg, respectively.

Figure 4A:
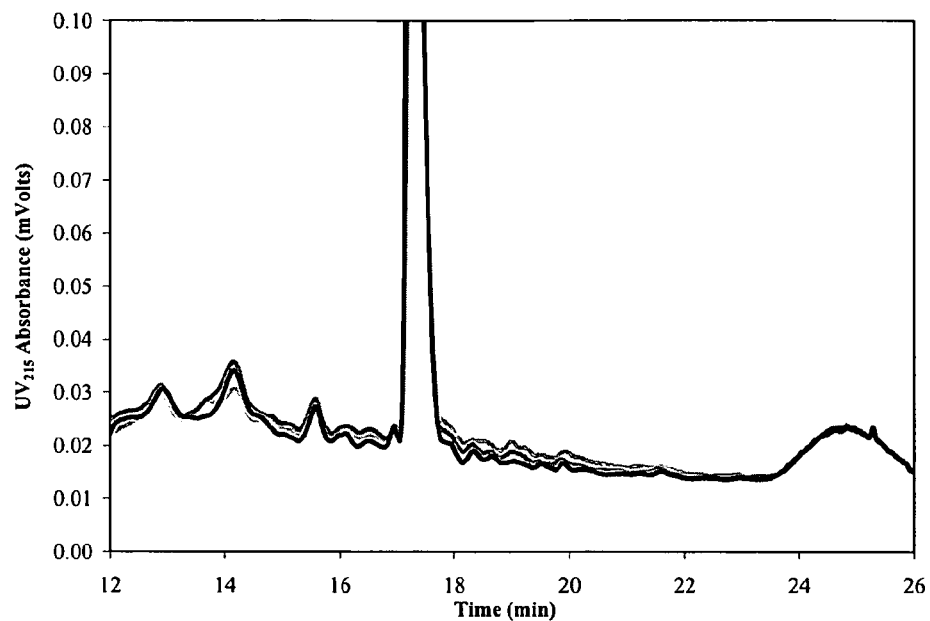
FIG. 4: Varying the ratio of EP-B2 and SC PEP in a two-enzyme combination glutenase. HPLC traces correspond to protein from whole wheat bread that has been treated with varying amounts of EP-B2 and SC PEP. (a) The following HPLC traces are presented: EP-B2 (30 units)+SC PEP (0.5 units) (—) EP-B2 (100 units)+SC PEP (0.5 units) (—); and EP-B2 (200 units)+SC PEP (0.5 units) (—). (b) The following HPLC traces are presented: EP-B2 (10 units per mg protein)+SC PEP (0.17 units per mg protein) (—); EP-B2 (10 units)+SC PEP (1.67 units) (—); EP-B2 (30 units)+SC PEP (0.17 units) (—); and EP-B2 (30 units)+SC PEP (1.67 units) (—). All digests included 0.6 mg/ml pepsin, and were performed for 60 min under the simulated gastric conditions described below. Standard peaks are defined in the description of FIG. 3, above.

Remarkably, at EP-B2 doses of 30-200 units per mg bread protein, an SC PEP dose of 0.5 units was adequate to neutralize any advantage associated with EP-B2 dose escalation (FIG. 4a). This observation vividly illustrates the synergistic potential of the two enzymes; addition of one weight equivalent of SC PEP to EP-B2 enhances the gluten detoxification capacity of EP-B2 more significantly than simply doubling the EP-B2 dose. This may result from the highly complementary substrate specificity of the two enzymes, both with respect to chain length and amino acid sequence.

Figure 4B:
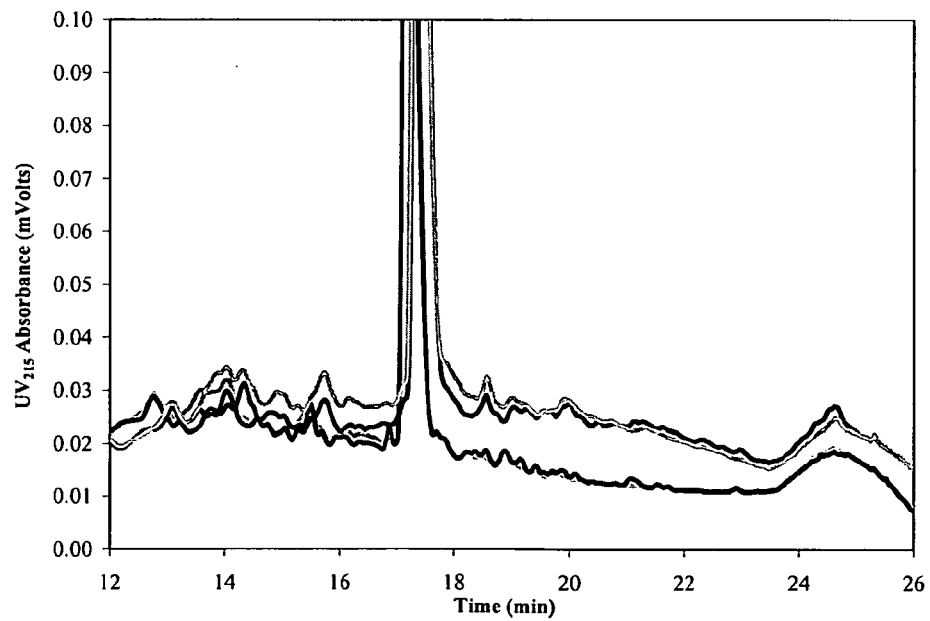

The influence of SC PEP on the gluten detoxification ability of EP-B2 at doses lower than 30 units per mg bread protein is illustrated in FIG. 4b. When the EP-B2 dose is reduced from 30 units/mg protein to 10 units/mg protein, the activity of this enzyme limits the overall gluten detoxification capacity of the combination agent, and merely increasing SC PEP dose has minimal effect. Longer gluten peptides may accumulate at sub-critical EP-B2:gluten ratios, thereby limiting the synergistic potential of SC PEP in the two-enzyme glutenase combination.

Figure 5:
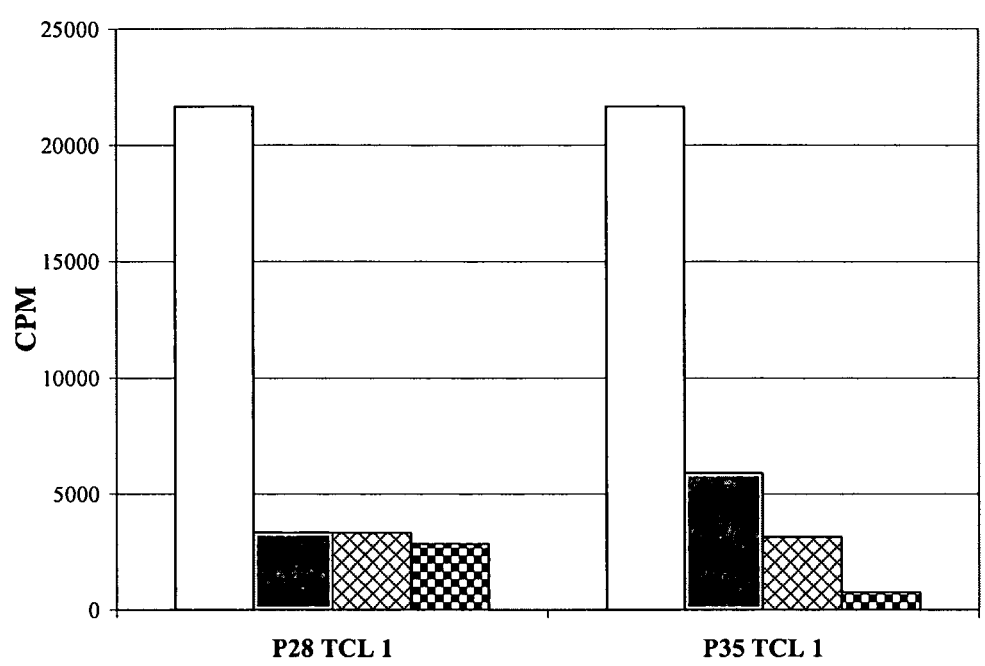
FIG. 5: T cell analysis of whole wheat bread samples treated with varying ratios of EP-B2 and SC PEP. Whole wheat bread was digested with a fixed amount of EP-B2 (30 units per mg bread protein) and varying levels of SC PEP. All digests were performed under simulated gastric conditions for 60 min at 37° C. with 0.6 mg/mL pepsin. T cell proliferation data, presented as [signal−(VAVY+T cells)], was obtained with two independently derived polyclonal T cell lines (P28 TCL1 and P35 TCL 1). Data is shown for the following samples: No SC PEP (clear); 0.17 SC PEP units per mg protein (shaded); 0.5 SC PEP units per mg protein (diagonal cross); and 1.67 SC PEP units per mg protein (checkerboard).

The HPLC results in FIG. 4 were verified via T cell proliferation and indirect competitive ELISA experiments (FIGS. 1 and 5; Table 1). As shown, addition of SC PEP to low or high EP-B2 doses reduces the level of gliadin epitopes and enhances the gluten detoxification capacity of EP-B2. At a fixed EP-B2 dose of 30 units/mg bread protein, the SC PEP dose was varied between 0.17-1.67 units (FIG. 5). Even the lowest SC PEP dose resulted in substantial immuno-detoxification of the gluten in whole wheat bread, as assessed by gluten responsive T cell lines from two celiac sprue patients. Additional SC PEP further reduced the proliferative potential of gluten against one of the T cell lines, while having virtually no impact on the other.

Figure 6:
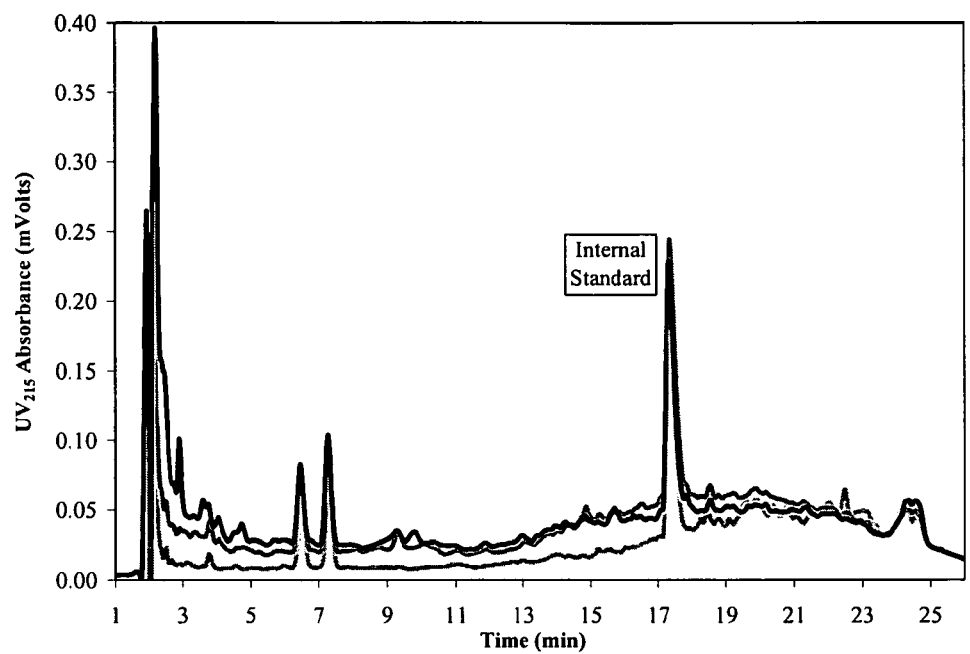
FIG. 6: Activity of EP-B2+SC PEP in rat stomach. Representative HPLC traces correspond to representative samples collected from the stomach of rats fed with whole wheat bread and the following enzymes: vehicle (—), EP-B2 (—), EP-B2+SC PEP (—). In each case (3 animals per cohort), animals were fed 4 g whole wheat bread and allowed to digest the meal for 120 min prior to euthanization. Gastric material was collected, stored, and analyzed as described below. Standard peaks are defined in the description of FIG. 3, above.

In Vivo Activity of the EP-B2+SC PEP Combination Glutenase:

The in vivo activity of the EP-B2+SC PEP combination was evaluated using a rodent model of gastric digestion, which had been used earlier to assess the glutenase activity of EP-B2 (Gass et al. J Pharmacol Exp Ther 2006; 318:1178-86). In this experiment, the liquid enzyme formulations (or appropriate buffers as vehicle) were added onto whole wheat bread and fed to fasted rats. At a specified time, the rats were euthanized. Their gastric contents were collected and analyzed via HPLC. Three rats were tested under each of three experimental conditions (vehicle, EP-B2 only, EP-B2+SC PEP). A representative set of results, all of which were very similar to analogous data obtained under in vitro conditions, is shown in FIG. 6. Addition of EP-B2 caused a marked increase in the area under the curve corresponding to gluten-derived oligopeptides (14-24 min retention time), while inclusion of SC PEP resulted in a further increase in the early eluting peptides, accompanied by a reduction in the oligopeptide region of the HPLC trace. These qualitative findings verify that EP-B2 and SC PEP can complement each other to digest gluten in whole wheat bread before it is emptied into the small intestine (i.e. the affected organ in Celiac sprue patients).

In Vitro Digestion of Whole Wheat Bread:

Whole wheat bread was digested in vitro using conditions that mimicked gastric and duodenal digestion, and the resulting samples were analyzed by HPLC. Previous in vitro digestion experiments with glutenases have focused exclusively on the digestion of uncooked whole gluten or gluten oligopeptides. As such, the in vitro digestion of the whole wheat bread was compared to the digestion of whole gluten.

During simulated gastric digestion of the whole wheat bread, only a small fraction of the gluten-derived protein is solubilized and resolved on the HPLC. The largest fraction is the broad peak that elutes ~25 min, which represents long gluten oligopeptides (>30 amino acids). For uncooked gluten, this late eluting peak is the dominant peak and is considerably more abundant than the corresponding peak from whole wheat bread. This suggests that, in contrast to uncooked gluten, whole wheat bread gluten digests more slowly under gastric conditions.

The treatment of the pepsin-treated bread under simulated duodenal conditions caused a significant increase in all of the peaks, especially gluten-derived oligopeptides that appear in the 15-23 min range. For uncooked gluten, the 25 min peak decreases whereas the earlier eluting peaks (15-23 min) increase. At the end of the 30 min duodenal digestion, both PTC-treated whole wheat bread and PTC-treated gluten had similar overall profiles, characterized by a series of peaks eluting from ~15-23 min, with a comparable late-eluting peak at ~25 min.

This example demonstrates that the properties of a a combination glutenase comprised of EP-B2 and SC PEP are ideal for the detoxification of gluten. A practical advantage of this combination product is that both enzymes are active and stable in the stomach, and can therefore be administered as lyophilized powders or simple capsules/tablets. In this combination, EP-B2 is primarily responsible for hydrolyzing complex gluten proteins at glutamine residues into relatively short (but still inflammatory) oligopeptides, whereas SC PEP breaks down these oligopeptides at internal proline residues to yield non-toxic metabolites.

Example 2

Selection of the Dose Ratio

Dose ratio variation studies utilized proEP-B2 and SC-PEP lots with specific activities of 5500 units/mg and 1270 units/mg, respectively, corresponding to an enzyme activity ratio of 4:1. To demonstrate the synergistic activity of the two enzymes and to establish an appropriate fixed-dose ratio for clinical investigation, varying amounts of enzymes were added to whole wheat bread. All experiments were performed under simulated gastric conditions (i.e., 1 g bread was incubated for 10-60 minutes at 37° C. with 6.67 mL 0.01 N HCl containing 0.6 mg/mL pepsin and an appropriate amount of enzymes). Samples were analyzed by reverse-phase HPLC under conditions that have been optimized to resolve the entire spectrum of peptides released via gastrointestinal hydrolysis of gluten. Under these analytical conditions, most immunotoxic peptides eluted at retention times higher than 12 minutes. For example, representative antigenic oligopeptides comprised of 9, 11, 12, 14, 21 and 28 residues elute at 12.5 minutes, 18.5 minutes, 21.5 minutes, 22.5 minutes and 22 minutes, respectively. The broad peak at 25 minutes includes longer gluten-derived peptides (>30 residues); for example, a highly immunogenic 33-mer peptide eluted at 25 minutes. Thus, in an HPLC tracing, the area under the curve between 12-26 minutes decreases as gluten was progressively detoxified, while the area under the curve between 2-10 minutes increased as gluten was detoxified.

Two important conclusions were drawn from the data summarized below, which were collected at a gluten:EP-B2 weight ratio of 75:1 (corresponding to ~50 mg EP-B2 consumed with one slice of bread). First, addition of SC-PEP to EP-B2 has a strong synergistic effect on gluten detoxification. Specifically, at a gluten:EP-B2:SC-PEP weight ratio of 75:1:1, gluten digestion was markedly superior to that observed at a gluten:EP-B2 weight ratio of 38:1. Indeed, more extensive gluten digestion was observed at a weight ratio of 75:1:0.25, as compared to simply doubling the EP-B2 dose.

Second, although gluten is more thoroughly broken down as the SC-PEP:EP-B2 ratio is increased, the incremental benefit of SC-PEP is nearly saturated at an EP-B2:SC-PEP weight ratio of 1:1. Therefore, a fixed-dose ratio of 4:1; or 5:3 (activity units) EP-B2:SC-PEP is optimal for gluten digestion into non-toxic fragments.

The data summarized above simulate the gastric exposure of one slice of bread to ~100 mg of the combination enzyme product. These conclusions have been at 2-fold lower, 4-fold lower as well as 2-fold higher enzyme doses. Preliminary in vivo studies in bread-fed rats have also confirmed the complementary activities of EP-B2 and SC PEP. Along these lines, EP-B2 activity has also been demonstrated in the stomach of cynomolgus monkeys.

Although no biological mechanism has been identified to date that allows dietary proteins to be absorbed intact across the intestinal epithelium, the systemic bioavailabilty of active EP-B2 and SC-PEP is a potential concern. A key factor that could affect systemic bioavailability of the enzymes is the stability of the protein in the gut lumen. To estimate the half-life of EP-B2 and SC-PEP in the upper small intestine, EP-B2 and SC-PEP were incubated in simulated intestinal fluid (formulation based on United States Pharmacopoeia) and the proteolytic digests analyzed using Western blots and antiserum specific to the two proteins. Whereas EP-B2 and SC-PEP were relatively stable in the absence of pancreatin, both proteins were efficiently degraded by pancreatin with half-lives less than 5 minutes. These results indicate that neither protein will survive long enough in the small intestine to be absorbed into the bloodstream.

What is claimed is:

1. A method of hydrolyzing gluten proteins to non-toxic metabolites, the method comprising contacting gluten-containing foodstuff with an enzyme composition comprising: a combination of *Sphingomonas capsulata* prolyl endopeptidase (SC-PEP) and cysteine endoprotease B, isoform 2 (EP-B2), wherein the ratio of EP-B2:SC-PEP is 1:1 by weight; in a dose of from 100 mg to 2000 mg total enzyme, wherein the effective dose hydrolyzes gluten proteins to yield non-toxic metabolites.

2. The method of claim 1, wherein EP-B2 is provided as a proenzyme form of EP-B2.

3. The method of claim 1, wherein the contacting is performed in vivo.

4. The method of claim 3, wherein the effective dose is administered in vivo prior to or concurrently with a gluten-containing foodstuff.

5. The method of claim 4, wherein the effective dose is orally administered.

6. The method of claim 1, wherein the contacting is performed in vitro.

7. The method of claim 1, wherein the enzymes are provided separately.

8. The method of claim 1, wherein the enzymes are provided in a combined formulation.

9. The method of claim 1, wherein the specific activity of SC-PEP is at least 500 U/mg, where 1 unit is defined as 1 μM p-nitroaniline released per minute from a chromogenic substrate Cbz-Gly-Pro-pNA at room temperature; and the specific activity of EP-B2 is at least 500 U/mg, wherein the specific activity of EP-B2 is defined by the activity of the mature enzyme form, where 1 unit is defined as 1 μM p-nitroaniline released per minute from a chromogenic substrate CBz-Phe-Arg-pNA at room temperature.

10. The method of claim 9, wherein SC-PEP has a specific activity of at least 1000 U/g, and EP-B2 has a specific activity of at least 1000 U/mg.

11. The method of claim 9, wherein SC-PEP has a specific activity of about 2500 Units/mg, and proEP-B2 has a specific activity of about 4000 Units/mg.

12. An enzyme composition comprising:

a combination of *Sphingomonas capsulata* prolyl endopeptidase (SC-PEP) and cysteine endoprotease B, isoform 2 (EP-B2), wherein the ratio of EP-62:SC-PEP is 1:1 by weight, in a dose of from 100 mg to 2000 mg enzyme.

13. The enzyme combination of claim 12, wherein EP-B2 is provided as a proenzyme form of EP-B2.

14. The enzyme composition of claim 13, wherein the enzymes are provided separately.

15. The enzyme composition of claim 13, wherein the enzymes are provided in a combined formulation.

16. The enzyme composition of claim 13, wherein the specific activity of SC-PEP is at least 500 U/mg, where 1 unit is defined as 1 μM p-nitroaniline released per minute from a chromogenic substrate Cbz-Gly-Pro-pNA at room temperature; and the specific activity of EP-B2 is at least 500 U/mg, wherein the specific activity of EP-B2 is defined by the activity of the mature enzyme form, where 1 unit is defined as 1 μM p-nitroaniline released per minute from a chromogenic substrate CBz-Phe-Arg-pNA at room temperature.

17. The enzyme combination of claim 16, wherein SC-PEP has a specific activity of at least 1000 U/g, and EP-B2 has a specific activity of at least 1000 U/mg.

18. The enzyme combination of claim 16, wherein SC-PEP has a specific activity of about 2500 Units/mg, and proEP-B2 has a specific activity of about 4000 Units/mg.

* * * * *

SEQUENCE LISTING

```
<160> NUMBER OF SEQ ID NOS: 5

<210> SEQ ID NO 1
<211> LENGTH: 401
<212> TYPE: PRT
<213> ORGANISM: Hordeum vulgare

<400> SEQUENCE: 1

Met Gly Ser Ser His His His His His Ser Ser Gly Leu Val Pro
1               5                   10                  15

Arg Gly Ser His Met Ala Ser Met Thr Gly Gly Asn Asn Met Gly Arg
            20                  25                  30

Asp Pro Cys Ser Ala Ile Pro Met Glu Asp Lys Asp Leu Glu Ser Glu
        35                  40                  45

Glu Ala Leu Trp Asp Leu Tyr Glu Arg Trp Gln Ser Ala His Arg Val
    50                  55                  60

Arg Arg His His Ala Glu Lys His Arg Arg Phe Gly Thr Phe Lys Ser
65                  70                  75                  80

Asn Ala His Phe Ile His Ser His Asn Lys Arg Gly Asp His Pro Tyr
                85                  90                  95

Arg Leu His Leu Asn Arg Phe Gly Asp Met Asp Gln Ala Glu Phe Arg
            100                 105                 110

Ala Thr Phe Val Gly Asp Leu Arg Arg Asp Thr Pro Ser Lys Pro Pro
        115                 120                 125

Ser Val Pro Gly Phe Met Tyr Ala Ala Leu Asn Val Ser Asp Leu Pro
    130                 135                 140

Pro Ser Val Asp Trp Arg Gln Lys Gly Ala Val Thr Gly Val Lys Asp
145                 150                 155                 160

Gln Gly Lys Cys Gly Ser Cys Trp Ala Phe Ser Thr Val Val Ser Val
```

```
                165                 170                 175
Glu Gly Ile Asn Ala Ile Arg Thr Gly Ser Leu Val Ser Leu Ser Glu
            180                 185                 190
Gln Glu Leu Ile Asp Cys Asp Thr Ala Asp Asn Asp Gly Cys Gln Gly
            195                 200                 205
Gly Leu Met Asp Asn Ala Phe Glu Tyr Ile Lys Asn Asn Gly Gly Leu
        210                 215                 220
Ile Thr Glu Ala Ala Tyr Pro Tyr Arg Ala Ala Arg Gly Thr Cys Asn
225                 230                 235                 240
Val Ala Arg Ala Ala Gln Asn Ser Pro Val Val His Ile Asp Gly
                245                 250                 255
His Gln Asp Val Pro Ala Asn Ser Glu Glu Asp Leu Ala Arg Ala Val
            260                 265                 270
Ala Asn Gln Pro Val Ser Val Ala Val Glu Ala Ser Gly Lys Ala Phe
        275                 280                 285
Met Phe Tyr Ser Glu Gly Val Phe Thr Gly Glu Cys Gly Thr Glu Leu
    290                 295                 300
Asp His Gly Val Ala Val Val Gly Tyr Gly Val Ala Glu Asp Gly Lys
305                 310                 315                 320
Ala Tyr Trp Thr Val Lys Asn Ser Trp Gly Pro Ser Trp Gly Glu Gln
                325                 330                 335
Gly Tyr Ile Arg Val Glu Lys Asp Ser Gly Ala Ser Gly Leu Cys
            340                 345                 350
Gly Ile Ala Met Glu Ala Ser Tyr Pro Val Lys Thr Tyr Ser Lys Pro
        355                 360                 365
Lys Pro Thr Pro Arg Arg Ala Leu Gly Ala Arg Glu Ser Leu Asn Ser
    370                 375                 380
Ser Ser Val Asp Lys Leu Ala Ala Ala Leu Glu His His His His His
385                 390                 395                 400
His

<210> SEQ ID NO 2
<211> LENGTH: 741
<212> TYPE: PRT
<213> ORGANISM: Sphingomonas capsulata

<400> SEQUENCE: 2

Met Val Ser Ser His His His His Ser Ser Gly Leu Val Pro
1               5                   10                  15
Arg Gly Ser Lys Asn Arg Leu Trp Leu Ala Met Ala Ala Pro Leu Ala
            20                  25                  30
Leu Ala Thr Pro Val Ala Phe Ala Gln Thr Pro Pro Thr Leu Ala Lys
        35                  40                  45
Asp Gln Ala Met Pro Ser Leu Pro Pro Tyr Pro Ala Ser Pro Gln Val
    50                  55                  60
Pro Leu Val Glu Asp His Phe Gly Glu Lys Val Ser Asp Pro Trp Arg
65                  70                  75                  80
Trp Leu Glu Ala Asp Val Arg Thr Asp Ala Lys Val Ala Ala Trp Val
                85                  90                  95
Gln Ala Gln Ser Ala Tyr Thr Ala Ala Tyr Leu Lys Gln Leu Pro Glu
            100                 105                 110
Arg Ala Ala Leu Glu Lys Arg Met Lys Ala Leu Ile Asp Tyr Glu Arg
        115                 120                 125
Phe Gly Leu Pro Gln Arg Arg Gly Ala Ser Val Phe Tyr Ser Trp Asn
```

-continued

```
            130                 135                 140
Ser Gly Leu Met Asn Gln Ser Gln Leu Leu Val Arg Pro Ala Asp Ala
145                 150                 155                 160

Pro Val Gly Thr Lys Gly Arg Val Leu Leu Asp Pro Asn Thr Trp Ala
                165                 170                 175

Lys Asp Gly Ala Thr Ala Leu Asp Ala Trp Ala Ala Ser Asp Asp Gly
                180                 185                 190

Arg Leu Leu Ala Tyr Ser Val Gln Asp Gly Gly Ser Asp Trp Arg Thr
                195                 200                 205

Val Lys Phe Val Gly Val Ala Asp Gly Lys Pro Leu Ala Asp Glu Leu
                210                 215                 220

Lys Trp Val Lys Phe Ser Gly Leu Ala Trp Leu Gly Asn Asp Ala Leu
225                 230                 235                 240

Leu Tyr Ser Arg Phe Ala Glu Pro Lys Glu Gly Gln Ala Phe Gln Ala
                245                 250                 255

Leu Asn Tyr Asn Gln Thr Val Trp Leu His Arg Leu Gly Thr Pro Gln
                260                 265                 270

Ser Ala Asp Gln Pro Val Phe Ala Thr Pro Glu Leu Pro Lys Arg Gly
                275                 280                 285

His Gly Ala Ser Val Ser Ser Asp Gly Arg Trp Val Val Ile Thr Ser
                290                 295                 300

Ser Glu Gly Thr Asp Pro Val Asn Thr Val His Val Ala Arg Val Thr
305                 310                 315                 320

Asn Gly Lys Ile Gly Pro Val Thr Ala Leu Ile Pro Asp Leu Lys Ala
                325                 330                 335

Gln Trp Asp Phe Val Asp Gly Val Gly Asp Gln Leu Trp Phe Val Ser
                340                 345                 350

Gly Asp Gly Ala Pro Leu Lys Lys Ile Val Arg Val Asp Leu Ser Gly
                355                 360                 365

Ser Thr Pro Arg Phe Asp Thr Val Val Pro Glu Ser Lys Asp Asn Leu
370                 375                 380

Glu Ser Val Gly Ile Ala Gly Asn Arg Leu Phe Ala Ser Tyr Ile His
385                 390                 395                 400

Asp Ala Lys Ser Gln Val Leu Ala Phe Asp Leu Asp Gly Lys Pro Ala
                405                 410                 415

Gly Ala Val Ser Leu Pro Gly Ile Gly Ser Ala Ser Gly Leu Ser Gly
                420                 425                 430

Arg Pro Gly Asp Arg His Ala Tyr Leu Ser Phe Ser Ser Phe Thr Gln
                435                 440                 445

Pro Ala Thr Val Leu Ala Leu Asp Pro Ala Thr Ala Lys Thr Thr Pro
450                 455                 460

Trp Glu Pro Val His Leu Thr Phe Asp Pro Asp Phe Arg Val Glu
465                 470                 475                 480

Gln Val Phe Tyr Pro Ser Lys Asp Gly Thr Lys Val Pro Met Phe Ile
                485                 490                 495

Val Arg Arg Lys Asp Ala Lys Gly Pro Leu Pro Thr Leu Leu Tyr Gly
                500                 505                 510

Tyr Gly Gly Phe Asn Val Ala Leu Thr Pro Trp Phe Ser Ala Gly Phe
                515                 520                 525

Met Thr Trp Ile Asp Ser Gly Gly Ala Phe Ala Leu Ala Asn Leu Arg
530                 535                 540

Gly Gly Gly Glu Tyr Gly Asp Ala Trp His Asp Ala Gly Arg Arg Asp
545                 550                 555                 560
```

```
Lys Lys Gln Asn Val Phe Asp Asp Phe Ile Ala Ala Gly Glu Trp Leu
                565                 570                 575

Ile Ala Asn Gly Val Thr Pro Arg His Gly Leu Ala Ile Glu Gly Gly
            580                 585                 590

Ser Asn Gly Gly Leu Leu Ile Gly Ala Val Thr Asn Gln Arg Pro Asp
        595                 600                 605

Leu Phe Ala Ala Ala Ser Pro Ala Val Gly Val Met Asp Met Leu Arg
    610                 615                 620

Phe Asp Gln Phe Thr Ala Gly Arg Tyr Trp Val Asp Tyr Gly Tyr
625                 630                 635                 640

Pro Glu Lys Glu Ala Asp Trp Arg Val Leu Arg Arg Tyr Ser Pro Tyr
                645                 650                 655

His Asn Val Arg Ser Gly Val Asp Tyr Pro Ala Ile Leu Val Thr Thr
            660                 665                 670

Ala Asp Thr Asp Asp Arg Val Val Pro Gly His Ser Leu Lys Tyr Thr
        675                 680                 685

Ala Ala Leu Gln Thr Ala Ala Ile Gly Pro Lys Pro His Leu Ile Arg
    690                 695                 700

Ile Glu Thr Arg Ala Gly His Gly Ser Gly Lys Pro Ile Asp Lys Gln
705                 710                 715                 720

Ile Glu Glu Thr Ala Asp Val Gln Ala Phe Leu Ala His Phe Thr Gly
                725                 730                 735

Leu Thr Pro Arg Pro
                740

<210> SEQ ID NO 3
<211> LENGTH: 348
<212> TYPE: PRT
<213> ORGANISM: Hordeum vulgare

<400> SEQUENCE: 3

Cys Ser Ala Ile Pro Met Glu Asp Lys Asp Leu Glu Ser Glu Glu Ala
1               5                   10                  15

Leu Trp Asp Leu Tyr Glu Arg Trp Gln Ser Ala His Arg Val Arg Arg
            20                  25                  30

His His Ala Glu Lys His Arg Arg Phe Gly Thr Phe Lys Ser Asn Ala
        35                  40                  45

His Phe Ile His Ser His Asn Lys Arg Gly Asp His Pro Tyr Arg Leu
    50                  55                  60

His Leu Asn Arg Phe Gly Asp Met Asp Gln Ala Glu Phe Arg Ala Thr
65                  70                  75                  80

Phe Val Gly Asp Leu Arg Arg Asp Thr Pro Ser Lys Pro Pro Ser Val
                85                  90                  95

Pro Gly Phe Met Tyr Ala Ala Leu Asn Val Ser Asp Leu Pro Pro Ser
            100                 105                 110

Val Asp Trp Arg Gln Lys Gly Ala Val Thr Gly Val Lys Asp Gln Gly
        115                 120                 125

Lys Cys Gly Ser Cys Trp Ala Phe Ser Thr Val Val Ser Val Glu Gly
    130                 135                 140

Ile Asn Ala Ile Arg Thr Gly Ser Leu Val Ser Leu Ser Glu Gln Glu
145                 150                 155                 160

Leu Ile Asp Cys Asp Thr Ala Asp Asn Asp Gly Cys Gln Gly Gly Leu
                165                 170                 175

Met Asp Asn Ala Phe Glu Tyr Ile Lys Asn Asn Gly Gly Leu Ile Thr
```

```
                180                 185                 190
Glu Ala Ala Tyr Pro Tyr Arg Ala Ala Arg Gly Thr Cys Asn Val Ala
            195                 200                 205

Arg Ala Ala Gln Asn Ser Pro Val Val His Ile Asp Gly His Gln
210                 215                 220

Asp Val Pro Ala Asn Ser Glu Glu Asp Leu Ala Arg Ala Val Ala Asn
225                 230                 235                 240

Gln Pro Val Ser Val Ala Val Glu Ala Ser Gly Lys Ala Phe Met Phe
            245                 250                 255

Tyr Ser Glu Gly Val Phe Thr Gly Glu Cys Gly Thr Glu Leu Asp His
            260                 265                 270

Gly Val Ala Val Val Gly Tyr Gly Val Ala Glu Asp Gly Lys Ala Tyr
            275                 280                 285

Trp Thr Val Lys Asn Ser Trp Gly Pro Ser Trp Gly Gln Gly Tyr
            290                 295                 300

Ile Arg Val Glu Lys Asp Ser Gly Ala Ser Gly Gly Leu Cys Gly Ile
305                 310                 315                 320

Ala Met Glu Ala Ser Tyr Pro Val Lys Thr Tyr Ser Lys Pro Lys Pro
                325                 330                 335

Thr Pro Arg Arg Ala Leu Gly Ala Arg Glu Ser Leu
                340                 345

<210> SEQ ID NO 4
<211> LENGTH: 243
<212> TYPE: PRT
<213> ORGANISM: Hordeum vulgare

<400> SEQUENCE: 4

Val Ser Asp Leu Pro Pro Ser Val Asp Trp Arg Gln Lys Gly Ala Val
1               5                   10                  15

Thr Gly Val Lys Asp Gln Gly Lys Cys Gly Ser Cys Trp Ala Phe Ser
            20                  25                  30

Thr Val Val Ser Val Glu Gly Ile Asn Ala Ile Arg Thr Gly Ser Leu
        35                  40                  45

Val Ser Leu Ser Glu Gln Glu Leu Ile Asp Cys Asp Thr Ala Asp Asn
    50                  55                  60

Asp Gly Cys Gln Gly Gly Leu Met Asp Asn Ala Phe Glu Tyr Ile Lys
65                  70                  75                  80

Asn Asn Gly Gly Leu Ile Thr Glu Ala Ala Tyr Pro Tyr Arg Ala Ala
                85                  90                  95

Arg Gly Thr Cys Asn Val Ala Arg Ala Ala Gln Asn Ser Pro Val Val
            100                 105                 110

Val His Ile Asp Gly His Gln Asp Val Pro Ala Asn Ser Glu Glu Asp
        115                 120                 125

Leu Ala Arg Ala Val Ala Asn Gln Pro Val Ser Val Ala Val Glu Ala
    130                 135                 140

Ser Gly Lys Ala Phe Met Phe Tyr Ser Glu Gly Val Phe Thr Gly Glu
145                 150                 155                 160

Cys Gly Thr Glu Leu Asp His Gly Val Ala Val Val Gly Tyr Gly Val
                165                 170                 175

Ala Glu Asp Gly Lys Ala Tyr Trp Thr Val Lys Asn Ser Trp Gly Pro
            180                 185                 190

Ser Trp Gly Glu Gln Gly Tyr Ile Arg Val Glu Lys Asp Ser Gly Ala
        195                 200                 205
```

Ser Gly Gly Leu Cys Gly Ile Ala Met Glu Ala Ser Tyr Pro Val Lys
210                 215                 220

Thr Tyr Ser Lys Pro Lys Pro Thr Pro Arg Arg Ala Leu Gly Ala Arg
225                 230                 235                 240

Glu Ser Leu

<210> SEQ ID NO 5
<211> LENGTH: 723
<212> TYPE: PRT
<213> ORGANISM: Sphingomonas capsulata

<400> SEQUENCE: 5

Ser Lys Asn Arg Leu Trp Leu Ala Met Ala Ala Pro Leu Ala Leu Ala
1               5                   10                  15

Thr Pro Val Ala Phe Ala Gln Thr Pro Pro Thr Leu Ala Lys Asp Gln
            20                  25                  30

Ala Met Pro Ser Leu Pro Pro Tyr Pro Ala Ser Pro Gln Val Pro Leu
        35                  40                  45

Val Glu Asp His Phe Gly Glu Lys Val Ser Asp Pro Trp Arg Trp Leu
50                  55                  60

Glu Ala Asp Val Arg Thr Asp Ala Lys Val Ala Ala Trp Val Gln Ala
65                  70                  75                  80

Gln Ser Ala Tyr Thr Ala Ala Tyr Leu Lys Gln Leu Pro Glu Arg Ala
                85                  90                  95

Ala Leu Glu Lys Arg Met Lys Ala Leu Ile Asp Tyr Glu Arg Phe Gly
            100                 105                 110

Leu Pro Gln Arg Arg Gly Ala Ser Val Phe Tyr Ser Trp Asn Ser Gly
        115                 120                 125

Leu Met Asn Gln Ser Gln Leu Leu Val Arg Pro Ala Asp Ala Pro Val
130                 135                 140

Gly Thr Lys Gly Arg Val Leu Leu Asp Pro Asn Thr Trp Ala Lys Asp
145                 150                 155                 160

Gly Ala Thr Ala Leu Asp Ala Trp Ala Ala Ser Asp Gly Arg Leu
                165                 170                 175

Leu Ala Tyr Ser Val Gln Asp Gly Gly Ser Asp Trp Arg Thr Val Lys
            180                 185                 190

Phe Val Gly Val Ala Asp Gly Lys Pro Leu Ala Asp Glu Leu Lys Trp
        195                 200                 205

Val Lys Phe Ser Gly Leu Ala Trp Leu Gly Asn Asp Ala Leu Leu Tyr
210                 215                 220

Ser Arg Phe Ala Glu Pro Lys Glu Gly Gln Ala Phe Gln Ala Leu Asn
225                 230                 235                 240

Tyr Asn Gln Thr Val Trp Leu His Arg Leu Gly Thr Pro Gln Ser Ala
                245                 250                 255

Asp Gln Pro Val Phe Ala Thr Pro Glu Leu Pro Lys Arg Gly His Gly
            260                 265                 270

Ala Ser Val Ser Ser Asp Gly Arg Trp Val Val Ile Thr Ser Ser Glu
        275                 280                 285

Gly Thr Asp Pro Val Asn Thr Val His Val Ala Arg Val Thr Asn Gly
290                 295                 300

Lys Ile Gly Pro Val Thr Ala Leu Ile Pro Asp Leu Lys Ala Gln Trp
305                 310                 315                 320

Asp Phe Val Asp Gly Val Gly Asp Gln Leu Trp Phe Val Ser Gly Asp
                325                 330                 335

```
Gly Ala Pro Leu Lys Lys Ile Val Arg Val Asp Leu Ser Gly Ser Thr
            340                 345                 350

Pro Arg Phe Asp Thr Val Val Pro Glu Ser Lys Asp Asn Leu Glu Ser
        355                 360                 365

Val Gly Ile Ala Gly Asn Arg Leu Phe Ala Ser Tyr Ile His Asp Ala
    370                 375                 380

Lys Ser Gln Val Leu Ala Phe Asp Leu Asp Gly Lys Pro Ala Gly Ala
385                 390                 395                 400

Val Ser Leu Pro Gly Ile Gly Ser Ala Ser Gly Leu Ser Gly Arg Pro
                405                 410                 415

Gly Asp Arg His Ala Tyr Leu Ser Phe Ser Ser Phe Thr Gln Pro Ala
            420                 425                 430

Thr Val Leu Ala Leu Asp Pro Ala Thr Ala Lys Thr Thr Pro Trp Glu
        435                 440                 445

Pro Val His Leu Thr Phe Asp Pro Ala Asp Phe Arg Val Glu Gln Val
    450                 455                 460

Phe Tyr Pro Ser Lys Asp Gly Thr Lys Val Pro Met Phe Ile Val Arg
465                 470                 475                 480

Arg Lys Asp Ala Lys Gly Pro Leu Pro Thr Leu Leu Tyr Gly Tyr Gly
                485                 490                 495

Gly Phe Asn Val Ala Leu Thr Pro Trp Phe Ser Ala Gly Phe Met Thr
            500                 505                 510

Trp Ile Asp Ser Gly Gly Ala Phe Ala Leu Ala Asn Leu Arg Gly Gly
        515                 520                 525

Gly Glu Tyr Gly Asp Ala Trp His Asp Ala Gly Arg Arg Asp Lys Lys
    530                 535                 540

Gln Asn Val Phe Asp Asp Phe Ile Ala Ala Gly Glu Trp Leu Ile Ala
545                 550                 555                 560

Asn Gly Val Thr Pro Arg His Gly Leu Ala Ile Glu Gly Gly Ser Asn
                565                 570                 575

Gly Gly Leu Leu Ile Gly Ala Val Thr Asn Gln Arg Pro Asp Leu Phe
            580                 585                 590

Ala Ala Ala Ser Pro Ala Val Gly Val Met Asp Met Leu Arg Phe Asp
        595                 600                 605

Gln Phe Thr Ala Gly Arg Tyr Trp Val Asp Asp Tyr Gly Tyr Pro Glu
    610                 615                 620

Lys Glu Ala Asp Trp Arg Val Leu Arg Arg Tyr Ser Pro Tyr His Asn
625                 630                 635                 640

Val Arg Ser Gly Val Asp Tyr Pro Ala Ile Leu Val Thr Thr Ala Asp
                645                 650                 655

Thr Asp Asp Arg Val Val Pro Gly His Ser Leu Lys Tyr Thr Ala Ala
            660                 665                 670

Leu Gln Thr Ala Ala Ile Gly Pro Lys Pro His Leu Ile Arg Ile Glu
        675                 680                 685

Thr Arg Ala Gly His Gly Ser Gly Lys Pro Ile Asp Lys Gln Ile Glu
    690                 695                 700

Glu Thr Ala Asp Val Gln Ala Phe Leu Ala His Phe Thr Gly Leu Thr
705                 710                 715                 720

Pro Arg Pro
```